(12) United States Patent
Parker et al.

(10) Patent No.: US 11,944,440 B2
(45) Date of Patent: *Apr. 2, 2024

(54) METHOD AND APPARATUS FOR ESTIMATING NEURAL RECRUITMENT

(71) Applicant: Saluda Medical Pty Ltd, Artarmon (AU)

(72) Inventors: John Louis Parker, Artarmon (AU); James Hamilton Wah, Artarmon (AU); Dean Michael Karantonis, Artarmon (AU); Peter Scott Vallack Single, Artarmon (AU)

(73) Assignee: Saluda Medical Pty Ltd, Artarmon (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/892,897

(22) Filed: Aug. 22, 2022

(65) Prior Publication Data
US 2024/0000358 A1    Jan. 4, 2024

Related U.S. Application Data

(63) Continuation of application No. 17/355,036, filed on Jun. 22, 2021, now Pat. No. 11,445,958, which is a
(Continued)

(30) Foreign Application Priority Data

| | | |
|---|---|---|
| May 13, 2011 | (AU) | 2011901817 |
| May 13, 2011 | (AU) | 2011901827 |

(51) Int. Cl.
*A61B 5/24*    (2021.01)
*A61N 1/05*    (2006.01)
*A61N 1/36*    (2006.01)

(52) U.S. Cl.
CPC .............. *A61B 5/24* (2021.01); *A61N 1/0551* (2013.01); *A61N 1/36071* (2013.01); *A61N 1/36135* (2013.01)

(58) Field of Classification Search
CPC .................. A61B 5/4041; A61B 5/04001; A61N 1/0551; A61N 1/36071; A61N 1/36135
See application file for complete search history.

(56) References Cited

U.S. PATENT DOCUMENTS

| | | |
|---|---|---|
| 3,724,467 A | 4/1973 | Avery et al. |
| 3,736,434 A | 5/1973 | Darrow |

(Continued)

FOREIGN PATENT DOCUMENTS

| | | |
|---|---|---|
| AU | 2013277009 | 1/2016 |
| CN | 103648583 | 3/2014 |

(Continued)

OTHER PUBLICATIONS

"Advanced Pain Therapy using Neurostimulation for Chronic Pain", Medtronic RestoreSensor clinical trial paper, Clinical summary, 2011-11, pp. 32.
(Continued)

*Primary Examiner* — Patrick Fernandes
(74) *Attorney, Agent, or Firm* — Barnes & Thornburg LLP

(57) ABSTRACT

An implantable device for estimating neural recruitment arising from a stimulus, has a plurality of electrodes. A stimulus source provides stimuli to be delivered from the electrodes to neural tissue. Measurement circuitry obtains a measurement of a neural signal sensed at the electrodes. A control unit is configured to control application of a selected stimulus to neural tissue using the stimulus electrodes; and after the selected neural stimulus, apply a probe stimulus having a short pulse width. A remnant neural response
(Continued)

evoked by the probe stimulus is measured; and the control unit estimates from the remnant neural response a neural recruitment caused by the selected neural stimulus.

29 Claims, 11 Drawing Sheets

Related U.S. Application Data continuation of application No. 15/928,040, filed on Mar. 21, 2018, now Pat. No. 11,045,129, which is a continuation of application No. 14/117,152, filed as application No. PCT/AU2012/000517 on May 11, 2012, now Pat. No. 9,974,455.

(56) References Cited

U.S. PATENT DOCUMENTS

| | | |
|---|---|---|
| 3,817,254 A | 6/1974 | Maurer |
| 3,898,472 A | 8/1975 | Long |
| 4,158,196 A | 6/1979 | Crawford, Jr. |
| 4,418,695 A | 12/1983 | Buffet |
| 4,474,186 A | 10/1984 | Ledley et al. |
| 4,628,934 A | 12/1986 | Pohndorf et al. |
| 4,807,643 A | 2/1989 | Rosier |
| 4,856,525 A | 8/1989 | van den Honert |
| 5,113,859 A | 5/1992 | Funke |
| 5,139,020 A | 8/1992 | Koestner et al. |
| 5,143,081 A | 9/1992 | Young et al. |
| 5,156,154 A | 10/1992 | Valenta et al. |
| 5,172,690 A | 12/1992 | Nappholz et al. |
| 5,184,615 A | 2/1993 | Nappholz et al. |
| 5,188,106 A | 2/1993 | Nappholz et al. |
| 5,215,100 A | 6/1993 | Spitz et al. |
| 5,324,311 A | 6/1994 | Acken |
| 5,417,719 A | 5/1995 | Hull et al. |
| 5,431,693 A | 7/1995 | Schroeppel |
| 5,458,623 A | 10/1995 | Lu et al. |
| 5,476,486 A | 12/1995 | Lu et al. |
| 5,497,781 A | 3/1996 | Chen et al. |
| 5,638,825 A | 6/1997 | Yamazaki et al. |
| 5,702,429 A | 12/1997 | King et al. |
| 5,758,651 A | 6/1998 | Nygaro et al. |
| 5,776,170 A | 7/1998 | Macdonald et al. |
| 5,785,651 A | 7/1998 | Kuhn et al. |
| 5,792,212 A | 8/1998 | Weijand et al. |
| 5,814,092 A | 9/1998 | King |
| 5,895,416 A | 4/1999 | Barreras et al. |
| 5,913,882 A | 6/1999 | King |
| 5,999,848 A | 12/1999 | Gord et al. |
| 6,020,857 A | 2/2000 | Podger |
| 6,027,456 A | 2/2000 | Feler et al. |
| 6,038,480 A | 3/2000 | Hrdlicka et al. |
| 6,066,163 A | 5/2000 | John |
| 6,114,164 A | 9/2000 | Dennis et al. |
| 6,144,881 A | 11/2000 | Hemming et al. |
| 6,157,861 A | 12/2000 | Faltys et al. |
| 6,212,431 B1 | 4/2001 | Hahn et al. |
| 6,246,912 B1 | 6/2001 | Sluijter et al. |
| 6,381,496 B1 | 4/2002 | Meadows et al. |
| 6,449,512 B1 | 9/2002 | Boveja |
| 6,463,328 B1 | 10/2002 | John |
| 6,473,649 B1 | 10/2002 | Gryzwa et al. |
| 6,473,653 B1 | 10/2002 | Schallhorn et al. |
| 6,493,576 B1 | 12/2002 | Dankwart-Eder |
| 6,516,227 B1 | 2/2003 | Meadows et al. |
| 6,522,932 B1 | 2/2003 | Kuzma |
| 6,600,955 B1 | 7/2003 | Zierhofer et al. |
| 6,658,293 B2 | 12/2003 | Vonk et al. |
| 6,675,046 B2 | 1/2004 | Holsheimer |
| 6,782,292 B2 | 8/2004 | Whitehurst |
| 6,895,280 B2 | 5/2005 | Meadows et al. |
| 6,898,582 B2 | 5/2005 | Lange et al. |
| 6,909,917 B2 | 6/2005 | Woods et al. |
| 7,089,059 B1 | 8/2006 | Pless |
| 7,171,261 B1 | 1/2007 | Litvak et al. |
| 7,177,675 B2 | 2/2007 | Suffin et al. |
| 7,206,640 B1 | 4/2007 | Overstreet |
| 7,231,254 B2 | 6/2007 | Dilorenzo et al. |
| 7,286,876 B2 | 10/2007 | Yonce et al. |
| 7,412,287 B2 | 8/2008 | Yonce et al. |
| 7,450,992 B1 | 11/2008 | Cameron |
| 7,634,315 B2 | 12/2009 | Cholette |
| 7,734,340 B2 | 6/2010 | De Ridder |
| 7,742,810 B2 | 6/2010 | Moffitt |
| 7,792,584 B2 | 9/2010 | Van et al. |
| 7,818,052 B2 | 10/2010 | Litvak et al. |
| 7,831,305 B2 | 11/2010 | Gliner |
| 7,835,804 B2 | 11/2010 | Fridman et al. |
| 7,890,182 B2 | 2/2011 | Parramon et al. |
| 7,894,905 B2 | 2/2011 | Pless et al. |
| 8,190,251 B2 | 5/2012 | Molnar et al. |
| 8,224,459 B1 | 7/2012 | Pianca et al. |
| 8,239,031 B2 | 8/2012 | Fried et al. |
| 8,249,698 B2 | 8/2012 | Mugler et al. |
| 8,332,047 B2 | 12/2012 | Libbus et al. |
| 8,359,102 B2 | 1/2013 | Thacker et al. |
| 8,417,342 B1 | 4/2013 | Abell |
| 8,454,529 B2 | 6/2013 | Daly et al. |
| 8,494,645 B2 | 7/2013 | Spitzer et al. |
| 8,515,545 B2 | 8/2013 | Trier |
| 8,538,541 B2 | 9/2013 | Milojevic et al. |
| 8,588,929 B2 | 11/2013 | Davis et al. |
| 8,620,459 B2 | 12/2013 | Gibson et al. |
| 8,655,002 B2 | 2/2014 | Parker |
| 8,670,830 B2 | 3/2014 | Carlson et al. |
| 8,886,323 B2 | 11/2014 | Wu et al. |
| 8,945,216 B2 | 2/2015 | Parker et al. |
| 9,044,155 B2 | 6/2015 | Strahl |
| 9,155,892 B2 | 10/2015 | Parker et al. |
| 9,302,112 B2 | 4/2016 | Bornzin et al. |
| 9,381,356 B2 | 7/2016 | Parker et al. |
| 9,386,934 B2 | 7/2016 | Parker et al. |
| 9,566,439 B2 | 2/2017 | Single et al. |
| 9,872,990 B2 | 1/2018 | Parker et al. |
| 9,974,455 B2 | 5/2018 | Parker et al. |
| 10,206,596 B2 | 2/2019 | Single et al. |
| 10,278,600 B2 | 5/2019 | Parker et al. |
| 10,368,762 B2 | 8/2019 | Single |
| 10,426,409 B2 | 10/2019 | Single |
| 10,500,399 B2 | 12/2019 | Single |
| 10,568,559 B2 | 2/2020 | Parker et al. |
| 10,588,524 B2 | 3/2020 | Single et al. |
| 10,588,698 B2 | 3/2020 | Parker et al. |
| 10,632,307 B2 | 4/2020 | Parker |
| 10,842,996 B2 | 11/2020 | Baru et al. |
| 10,849,525 B2 | 12/2020 | Parker et al. |
| 10,894,158 B2 | 1/2021 | Parker |
| 10,918,872 B2 | 2/2021 | Parker et al. |
| 11,006,846 B2 | 5/2021 | Parker et al. |
| 11,006,857 B2 | 5/2021 | Parker |
| 11,045,129 B2 | 6/2021 | Parker et al. |
| 11,110,270 B2 | 9/2021 | Parker et al. |
| 11,167,129 B2 | 11/2021 | Parker |
| 11,445,958 B2 | 9/2022 | Parker et al. |
| 2002/0055688 A1 | 5/2002 | Katims |
| 2002/0099419 A1 | 7/2002 | Ayal et al. |
| 2002/0193670 A1 | 12/2002 | Garfield et al. |
| 2003/0032889 A1 | 2/2003 | Wells |
| 2003/0045909 A1 | 3/2003 | Gross et al. |
| 2003/0139781 A1 | 7/2003 | Bradley et al. |
| 2003/0153959 A1 | 8/2003 | Thacker et al. |
| 2003/0195580 A1 | 10/2003 | Bradley et al. |
| 2004/0088017 A1 | 5/2004 | Sharma et al. |
| 2004/0122482 A1 | 6/2004 | Tung et al. |
| 2004/0158298 A1 | 8/2004 | Gliner |
| 2004/0225211 A1 | 11/2004 | Gozani et al. |
| 2004/0254494 A1 | 12/2004 | Spokoyny |
| 2005/0010265 A1 | 1/2005 | Baru Fassio et al. |
| 2005/0017190 A1 | 1/2005 | Eversmann et al. |
| 2005/0021104 A1 | 1/2005 | Dilorenzo |
| 2005/0065427 A1 | 3/2005 | Magill et al. |
| 2005/0070982 A1 | 3/2005 | Heruth et al. |

(56) References Cited

U.S. PATENT DOCUMENTS

| | | |
|---|---|---|
| 2005/0075683 A1 | 4/2005 | Miesel et al. |
| 2005/0101878 A1 | 5/2005 | Daly et al. |
| 2005/0107674 A1 | 5/2005 | Parthasarathy et al. |
| 2005/0113877 A1 | 5/2005 | Giardiello et al. |
| 2005/0137670 A1 | 6/2005 | Christopherson et al. |
| 2005/0149154 A1 | 7/2005 | Cohen |
| 2005/0192567 A1 | 9/2005 | Katims |
| 2005/0203600 A1 | 9/2005 | Wallace |
| 2005/0209655 A1 | 9/2005 | Kovacs et al. |
| 2005/0282149 A1 | 12/2005 | Royle et al. |
| 2006/0009820 A1 | 1/2006 | Gozani et al. |
| 2006/0020291 A1 | 1/2006 | Libbus et al. |
| 2006/0135998 A1 | 6/2006 | Bradley et al. |
| 2006/0195159 A1 | 8/2006 | Tass |
| 2006/0217782 A1 | 9/2006 | Boveja et al. |
| 2006/0264752 A1 | 11/2006 | Rubinsky et al. |
| 2006/0276722 A1 | 12/2006 | Litvak et al. |
| 2006/0287609 A1 | 12/2006 | Litvak et al. |
| 2007/0021800 A1 | 1/2007 | Bradley et al. |
| 2007/0073354 A1 | 3/2007 | Knudson et al. |
| 2007/0100378 A1 | 5/2007 | Maschino |
| 2007/0178579 A1 | 8/2007 | Ross et al. |
| 2007/0185409 A1 | 8/2007 | Wu et al. |
| 2007/0208394 A1 | 9/2007 | King et al. |
| 2007/0225765 A1 | 9/2007 | King |
| 2007/0225767 A1 | 9/2007 | Daly et al. |
| 2007/0244410 A1 | 10/2007 | Fridman et al. |
| 2007/0250120 A1 | 10/2007 | Flach et al. |
| 2007/0255372 A1 | 11/2007 | Metzler et al. |
| 2007/0282217 A1 | 12/2007 | McGinnis et al. |
| 2007/0287931 A1 | 12/2007 | Dilorenzo |
| 2008/0021292 A1 | 1/2008 | Stypulkowski |
| 2008/0051647 A1 | 2/2008 | Wu et al. |
| 2008/0064947 A1 | 3/2008 | Heruth et al. |
| 2008/0077191 A1 | 3/2008 | Morrell |
| 2008/0097529 A1 | 4/2008 | Parramon et al. |
| 2008/0132964 A1 | 6/2008 | Cohen et al. |
| 2008/0147155 A1 | 6/2008 | Swoyer |
| 2008/0183076 A1 | 7/2008 | Witte et al. |
| 2008/0208304 A1 | 8/2008 | Zdravkovic et al. |
| 2008/0234780 A1 | 9/2008 | Smith et al. |
| 2008/0275527 A1 | 11/2008 | Greenberg et al. |
| 2008/0294221 A1 | 11/2008 | Kilgore |
| 2008/0300655 A1 | 12/2008 | Chelette |
| 2008/0319508 A1 | 12/2008 | Botros et al. |
| 2009/0030337 A1 | 1/2009 | Gozani et al. |
| 2009/0033486 A1 | 2/2009 | Costantino et al. |
| 2009/0058635 A1 | 3/2009 | Lalonde et al. |
| 2009/0082691 A1 | 3/2009 | Denison et al. |
| 2009/0149912 A1 | 6/2009 | Dacey |
| 2009/0157155 A1 | 6/2009 | Bradley |
| 2009/0270957 A1 | 10/2009 | Pianca |
| 2009/0281594 A1 | 11/2009 | King et al. |
| 2009/0287277 A1 | 11/2009 | Conn et al. |
| 2009/0299214 A1 | 12/2009 | Wu et al. |
| 2009/0306491 A1 | 12/2009 | Haggers |
| 2009/0306533 A1 | 12/2009 | Rousche et al. |
| 2010/0010388 A1 | 1/2010 | Panken et al. |
| 2010/0057159 A1 | 3/2010 | Lozano |
| 2010/0058126 A1 | 3/2010 | Chang et al. |
| 2010/0069835 A1 | 3/2010 | Parker |
| 2010/0069996 A1 | 3/2010 | Strahl |
| 2010/0070007 A1 | 3/2010 | Parker |
| 2010/0070008 A1 | 3/2010 | Parker |
| 2010/0100153 A1 | 4/2010 | Carlson et al. |
| 2010/0106231 A1 | 4/2010 | Torgerson |
| 2010/0114237 A1 | 5/2010 | Giftakis et al. |
| 2010/0114258 A1 | 5/2010 | Donofrio et al. |
| 2010/0125313 A1 | 5/2010 | Lee et al. |
| 2010/0125314 A1 | 5/2010 | Bradley et al. |
| 2010/0145222 A1 | 6/2010 | Brunnett et al. |
| 2010/0152808 A1 | 6/2010 | Boggs |
| 2010/0179626 A1 | 7/2010 | Pilarski |
| 2010/0191307 A1 | 7/2010 | Fang et al. |
| 2010/0204748 A1 | 8/2010 | Lozano et al. |
| 2010/0222844 A1 | 9/2010 | Troosters et al. |
| 2010/0222858 A1 | 9/2010 | Meloy |
| 2010/0249643 A1 | 9/2010 | Gozani et al. |
| 2010/0249867 A1 | 9/2010 | Wanasek |
| 2010/0258342 A1 | 10/2010 | Parker |
| 2010/0262208 A1 | 10/2010 | Parker |
| 2010/0262214 A1 | 10/2010 | Robinson |
| 2010/0280570 A1 | 11/2010 | Sturm et al. |
| 2010/0286748 A1 | 11/2010 | Midani et al. |
| 2010/0331604 A1 | 12/2010 | Okamoto et al. |
| 2010/0331926 A1 | 12/2010 | Lee et al. |
| 2011/0004207 A1 | 1/2011 | Wallace et al. |
| 2011/0021943 A1 | 1/2011 | Lacour et al. |
| 2011/0028859 A1 | 2/2011 | Chian |
| 2011/0040546 A1 | 2/2011 | Gerber et al. |
| 2011/0077712 A1 | 3/2011 | Killian |
| 2011/0087085 A1 | 4/2011 | Tsampazis et al. |
| 2011/0093042 A1 | 4/2011 | Torgerson et al. |
| 2011/0106100 A1 | 5/2011 | Bischoff |
| 2011/0184488 A1 | 7/2011 | De Ridder et al. |
| 2011/0204811 A1 | 8/2011 | Pollmann-retsch |
| 2011/0224665 A1 | 9/2011 | Crosby et al. |
| 2011/0224749 A1 | 9/2011 | Ben-David et al. |
| 2011/0264165 A1 | 10/2011 | Molnar et al. |
| 2011/0270343 A1 | 11/2011 | Buschman et al. |
| 2011/0307030 A1 | 12/2011 | John |
| 2011/0313310 A1 | 12/2011 | Tomita |
| 2011/0313483 A1 | 12/2011 | Hincapie et al. |
| 2012/0029377 A1 | 2/2012 | Polak |
| 2012/0059275 A1 | 3/2012 | Fagin et al. |
| 2012/0101552 A1 | 4/2012 | Lazarewicz et al. |
| 2012/0101826 A1 | 4/2012 | Visser et al. |
| 2012/0109004 A1 | 5/2012 | Cadwell |
| 2012/0109236 A1 | 5/2012 | Jacobson et al. |
| 2012/0155183 A1 | 6/2012 | Aritome |
| 2012/0185020 A1 | 7/2012 | Simon et al. |
| 2012/0245481 A1 | 9/2012 | Blanco et al. |
| 2012/0253423 A1 | 10/2012 | Youn et al. |
| 2012/0277621 A1 | 11/2012 | Gerber et al. |
| 2012/0277823 A1 | 11/2012 | Gerber et al. |
| 2012/0310301 A1 | 12/2012 | Bennett et al. |
| 2013/0041449 A1 | 2/2013 | Cela et al. |
| 2013/0053722 A1 | 2/2013 | Carlson et al. |
| 2013/0060302 A1 | 3/2013 | Polefko et al. |
| 2013/0172774 A1 | 7/2013 | Crowder et al. |
| 2013/0268043 A1 | 10/2013 | Tasche et al. |
| 2013/0289661 A1 | 10/2013 | Griffith et al. |
| 2013/0289683 A1 | 10/2013 | Parker et al. |
| 2014/0046407 A1 | 2/2014 | Ben-Ezra et al. |
| 2014/0066803 A1 | 3/2014 | Choi |
| 2014/0142447 A1 | 5/2014 | Takahashi et al. |
| 2014/0194771 A1 | 7/2014 | Parker et al. |
| 2014/0194772 A1 | 7/2014 | Single et al. |
| 2014/0236042 A1 | 8/2014 | Parker et al. |
| 2014/0236257 A1 | 8/2014 | Parker et al. |
| 2014/0243926 A1 | 8/2014 | Carcieri |
| 2014/0243931 A1 | 8/2014 | Parker et al. |
| 2014/0249396 A1 | 9/2014 | Shacham-Diamand et al. |
| 2014/0276195 A1 | 9/2014 | Papay et al. |
| 2014/0277250 A1 | 9/2014 | Su et al. |
| 2014/0277267 A1 | 9/2014 | Vansickle et al. |
| 2014/0288551 A1 | 9/2014 | Bharmi et al. |
| 2014/0288577 A1 | 9/2014 | Robinson et al. |
| 2014/0296737 A1 | 10/2014 | Parker et al. |
| 2014/0324118 A1 | 10/2014 | Simon et al. |
| 2014/0350634 A1 | 11/2014 | Grill et al. |
| 2014/0358024 A1 | 12/2014 | Nelson et al. |
| 2015/0018699 A1 | 1/2015 | Zeng et al. |
| 2015/0025597 A1 | 1/2015 | Surth |
| 2015/0051637 A1 | 2/2015 | Osorio |
| 2015/0148869 A1 | 5/2015 | Dorvall et al. |
| 2015/0164354 A1 | 6/2015 | Parker et al. |
| 2015/0174396 A1 | 6/2015 | Fisher et al. |
| 2015/0238104 A1 | 8/2015 | Tass |
| 2015/0238304 A1 | 8/2015 | Lamroui |
| 2015/0282725 A1 | 10/2015 | Single |
| 2015/0313487 A1 | 11/2015 | Single |
| 2015/0360031 A1 | 12/2015 | Bornzin et al. |
| 2015/0374999 A1 | 12/2015 | Parker |

(56) References Cited

U.S. PATENT DOCUMENTS

| | | | |
|---|---|---|---|
| 2016/0082265 A1 | 3/2016 | Moffitt et al. |
| 2016/0082268 A1 | 3/2016 | Hershey et al. |
| 2016/0101289 A1 | 4/2016 | Stolen et al. |
| 2016/0106980 A1 | 4/2016 | Surth et al. |
| 2016/0121124 A1 | 5/2016 | Johanek et al. |
| 2016/0129272 A1 | 5/2016 | Hou et al. |
| 2016/0144189 A1 | 5/2016 | Bakker et al. |
| 2016/0166164 A1 | 6/2016 | Obradovic et al. |
| 2016/0175594 A1 | 6/2016 | Min et al. |
| 2016/0287126 A1 | 10/2016 | Parker et al. |
| 2016/0287182 A1 | 10/2016 | Single |
| 2016/0367808 A9 | 12/2016 | Simon et al. |
| 2017/0001017 A9 | 1/2017 | Parker et al. |
| 2017/0049345 A1 | 2/2017 | Single |
| 2017/0071490 A1 | 3/2017 | Parker et al. |
| 2017/0135624 A1 | 5/2017 | Parker |
| 2017/0157410 A1 | 6/2017 | Moffitt et al. |
| 2017/0173326 A1 | 6/2017 | Bloch et al. |
| 2017/0173335 A1 | 6/2017 | Min et al. |
| 2017/0173341 A1 | 6/2017 | Johanek et al. |
| 2017/0216587 A1 | 8/2017 | Parker |
| 2017/0361101 A1 | 12/2017 | Single |
| 2018/0071513 A1 | 3/2018 | Weiss et al. |
| 2018/0104493 A1 | 4/2018 | Doan et al. |
| 2018/0110987 A1 | 4/2018 | Parker |
| 2018/0117335 A1 | 5/2018 | Parker et al. |
| 2018/0132747 A1 | 5/2018 | Parker et al. |
| 2018/0132760 A1 | 5/2018 | Parker |
| 2018/0133459 A1 | 5/2018 | Parker et al. |
| 2018/0228391 A1 | 8/2018 | Parker et al. |
| 2018/0228547 A1 | 8/2018 | Parker |
| 2018/0229046 A1 | 8/2018 | Parker et al. |
| 2018/0256052 A1 | 9/2018 | Parker et al. |
| 2019/0001139 A1 | 1/2019 | Mishra et al. |
| 2019/0030339 A1 | 1/2019 | Baru et al. |
| 2019/0125269 A1 | 5/2019 | Markovic et al. |
| 2019/0168000 A1 | 6/2019 | Laird-Wah |
| 2019/0216343 A1 | 7/2019 | Single et al. |
| 2019/0239768 A1 | 8/2019 | Karantonis et al. |
| 2019/0307341 A1 | 10/2019 | Parker et al. |
| 2019/0357788 A1 | 11/2019 | Single |
| 2020/0029914 A1 | 1/2020 | Single |
| 2020/0129108 A1 | 4/2020 | Parker et al. |
| 2020/0155240 A1 | 5/2020 | Parker et al. |
| 2020/0215331 A1 | 7/2020 | Single |
| 2020/0282208 A1 | 9/2020 | Parker |
| 2021/0001133 A1 | 1/2021 | Williams et al. |
| 2021/0016091 A1 | 1/2021 | Parker et al. |
| 2021/0121696 A1 | 4/2021 | Parker et al. |
| 2021/0162214 A1 | 6/2021 | Parker |
| 2021/0267518 A1 | 9/2021 | Parker et al. |
| 2021/0308449 A1 | 10/2021 | Parker |
| 2021/0315502 A1 | 10/2021 | Parker et al. |

FOREIGN PATENT DOCUMENTS

| | | |
|---|---|---|
| CN | 103654762 | 3/2014 |
| CN | 103842022 | 6/2014 |
| CN | 104411360 | 3/2015 |
| EP | 0219084 | 4/1987 |
| EP | 1244496 | 10/2002 |
| EP | 0998958 | 8/2005 |
| EP | 2019716 | 11/2007 |
| EP | 2243510 | 10/2010 |
| EP | 2443995 | 4/2012 |
| EP | 2520327 | 11/2012 |
| EP | 2707095 | 3/2014 |
| EP | 3229893 | 10/2017 |
| JP | 2006504494 | 2/2006 |
| JP | 2009512505 | 3/2009 |
| JP | 2012524629 | 10/2012 |
| JP | 2013500779 | 1/2013 |
| JP | 2013527784 | 7/2013 |
| JP | 2013536044 | 3/2014 |
| JP | 2014522261 | 9/2014 |
| JP | 2014523261 | 9/2014 |
| WO | WO 1983003191 | 9/1983 |
| WO | WO 1993001863 | 2/1993 |
| WO | WO 1996012383 | 4/1996 |
| WO | WO 2000002623 | 1/2000 |
| WO | WO 2002036003 | 11/2001 |
| WO | WO 2002038031 | 5/2002 |
| WO | WO 2002049500 | 6/2002 |
| WO | WO 2002082982 | 10/2002 |
| WO | WO 2003028521 | 4/2003 |
| WO | WO 2003043690 | 5/2003 |
| WO | WO 2003103484 | 12/2003 |
| WO | WO 2004021885 | 3/2004 |
| WO | WO 2004103455 | 12/2004 |
| WO | WO 2005032656 | 4/2005 |
| WO | WO 2005105202 | 11/2005 |
| WO | WO 2005122887 | 12/2005 |
| WO | WO 2006091636 | 8/2006 |
| WO | WO 2007050657 | 5/2007 |
| WO | WO 2007064936 | 6/2007 |
| WO | WO 2007127926 | 11/2007 |
| WO | WO 2007130170 | 11/2007 |
| WO | WO 2008004204 | 1/2008 |
| WO | WO 2008049199 | 5/2008 |
| WO | WO 2009002072 | 12/2008 |
| WO | WO 2009002579 | 12/2008 |
| WO | WO 2009010870 | 1/2009 |
| WO | WO 2009130515 | 10/2009 |
| WO | WO 2009146427 | 12/2009 |
| WO | WO 2010013170 | 2/2010 |
| WO | WO 2010044989 | 4/2010 |
| WO | WO 2010051392 | 5/2010 |
| WO | WO 2010051406 | 5/2010 |
| WO | WO 2010057046 | 5/2010 |
| WO | WO 2010124139 | 10/2010 |
| WO | WO 2010138915 | 12/2010 |
| WO | WO 2011011327 | 1/2011 |
| WO | WO 2011014570 | 2/2011 |
| WO | WO 2011017778 | 2/2011 |
| WO | WO 2011066477 | 6/2011 |
| WO | WO 2011066478 | 6/2011 |
| WO | WO 2011112843 | 9/2011 |
| WO | WO 2011119251 | 9/2011 |
| WO | WO 2011159545 | 12/2011 |
| WO | WO 2012027252 | 3/2012 |
| WO | WO 2012027791 | 3/2012 |
| WO | WO 2012155183 | 11/2012 |
| WO | WO 2012155184 | 11/2012 |
| WO | WO 2012155185 | 11/2012 |
| WO | WO 2012155187 | 11/2012 |
| WO | WO 2012155188 | 11/2012 |
| WO | WO 2012155189 | 11/2012 |
| WO | WO 2012155190 | 11/2012 |
| WO | WO 2012162349 | 11/2012 |
| WO | WO 2013063111 | 5/2013 |
| WO | WO 2013075171 | 5/2013 |
| WO | WO 2014071445 | 5/2014 |
| WO | WO 2014071446 | 5/2014 |
| WO | WO 2014143577 | 9/2014 |
| WO | WO 2014150001 | 9/2014 |
| WO | WO 2015070281 | 5/2015 |
| WO | WO 2015074121 | 5/2015 |
| WO | WO 2015109239 | 7/2015 |
| WO | WO 2015143509 | 10/2015 |
| WO | WO 2015168735 | 11/2015 |
| WO | WO 2016011512 | 1/2016 |
| WO | WO 2016048974 | 3/2016 |
| WO | WO 2016059556 | 4/2016 |
| WO | WO 2016077882 | 5/2016 |
| WO | WO 2016090420 | 6/2016 |
| WO | WO 2016090436 | 6/2016 |
| WO | WO 2016115596 | 7/2016 |
| WO | WO 2016161484 | 10/2016 |
| WO | WO 2016168798 | 10/2016 |
| WO | WO 2016191807 | 12/2016 |
| WO | WO 2016191808 | 12/2016 |
| WO | WO 2016191815 | 12/2016 |
| WO | WO 2017053504 | 3/2017 |
| WO | WO 2017142948 | 8/2017 |

(56) References Cited

FOREIGN PATENT DOCUMENTS

| WO | WO 2017173493 | 10/2017 |
|----|---------------|---------|
| WO | WO 2017210352 | 12/2017 |
| WO | WO 2017219096 | 12/2017 |
| WO | WO 2018080753 | 5/2018 |
| WO | WO 2018119220 | 6/2018 |
| WO | WO 2018160992 | 9/2018 |
| WO | WO 2018170141 | 9/2018 |
| WO | WO 2019178634 | 9/2019 |
| WO | WO 2019204884 | 10/2019 |
| WO | WO 2019231796 | 12/2019 |
| WO | WO 2020082118 | 4/2020 |
| WO | WO 2020082126 | 4/2020 |
| WO | WO 2020082128 | 4/2020 |
| WO | WO 2020087123 | 5/2020 |
| WO | WO 2020087135 | 5/2020 |

OTHER PUBLICATIONS

"Battelle Neurotechnology—Moving Beyond The Limits in Neurotechnology", Battelle, www.battelle.org, May 2014, pp. 1-2.
"Evoke 12C Percutaneous Leads", Saluda Medical, specifications available in the "Evoke Surgical Guide", version 6, http://www.saludamedical.com/manuals/, retrieved May 2017.
"Haptic technology", Wikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
"Neural Bypass Technology Enables Movement in Paralyzed Patient", Posted on Jul. 29, 2014, 6 a.m. in Brain chips/computer interface, pp. 1-2.
"Percutaneous Lead Kit", St. Jude Medical Clinician's Manual, Models 3143, 3146, 3149, 3153, 3156, 3159, 3183, 3186, 3189, published Sep. 2016, 24 pages.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Abrard et al., "A time-frequency blindsignal separation methodapplicable to underdetermined mixtures of dependent sources", Signal Processing 85 (2005) 1389-1403.
Alam et al., "Evaluation of optimal electrode configurations for epidural spinal cord stimulation in cervical spinal cord injured rats", Journal of Neuroscience Methods, Mar. 2015, 28 pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
Andreassen et al., "Muscle Fibre Conduction Velocity in Motor Units of the Human Anterior Tibial Muscle: a New Size Principle Parameter", J. Physiol, (1987), 391, pp. 561-571.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Australian Examination Report for Application No. 2019283936, dated Apr. 1, 2021, 7 pages.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
Baltuch et al., "Deep brain stimulation for Parkinson's disease", CRC Press, 2007, 108.
Balzer et al., "Localization of cervical and cervicomedullary stimulation leads for pain treatment using median nerve somatosensay evoked potential collision testing", Journal of Neurosurgery, Jan. 2011, vol. 114, No. 1: pp. 200-205.
Blum, A. R. "An Electronic System for Extracellular Neural Stimulation and Recording", Dissertation, Georgia Institute of Technology, Aug. 2007, Retrieved from http://smartech.gatech.edu/handle/1853/16192 on Jan. 30, 2012.
Borg et al., "Conduction velocity and refractory period of single motor nerve fibres in antecedent poliomyelitis", Journal of Neurology, Neurosurgery, and Psychiatry, vol. 50, 1987, 443-446.
Bratta et al., "Orderly Stimulation of Skeletal Muscle Motor Units with Tripolar Nerve Cuff Electrode", IEEE Transactions on Biomedical Engineering, vol. 36, No. 8, 1989, pp. 836-843.
Brown et al., "Impact of Deep Brain Stimulation on Upper Limb Askinesia in Parkinson's Disease", Annals of Neurology, 45, No. 4, 1999, pp. 4 73-488.
Budagavi et al., "Modelling of compound nerve action potentials health and disease", Engineering in Medicine and Biology Society, 1992 14th Annual International Conference of the IEEE. vol. 6. IEEE, 1992. pp. 2600-2601.
Casey et al., "Separation of Mixed Audio Sources by Independent Subspace Analysis", Mitsubishi Electric Research Laboratories (2001), 8 pgs.
Celestin et al., "Pretreatment Psychosocial Variables as Predictors of Outcomes Following Lumbar Surgery and Spinal Cord Stimulation: A Systematic Review and Literature Synthesis", American Academy of Pain Medicine, 2009, vol. 10, No. 4, pp. 639-653. doi: 10.1111/j.1526-4637.2009.00632.X.
Cong et al., "A 32-channel modular bi-directional neural interface system with embedded DSP for closed-loop operation", 40th European Solid State Circuits Conference (ESSCIRC), 2014, pp. 99-102.
Connolly et al., "Towards a platform for prototyping control systems for optimization of neuromodulation therapies", IEEE Biomedical Circuits and Systems Conference (BioCAS), 2015, pp. 1-4.
Coquery et al., "Backward and forward masking in the perception of cutaneous stimuli", Perception & Psychophysics, 1973, vol. 13.No. 2, pp. 161-163.
Dawson, G. D., "The relative excitability and conduction velocity of sensory and motor nerve fibres in man", Journal of Physiology, 1956, vol. 131(2), pp. 436-451.
De Ridder et al., "Burst Spinal Cord Stimulation toward Paresthesia-Free Pain Suppression", Nuerosurgery-online.com, May 2010, vol. 66, No. 8, pp. 986-990.
Delgado et al., "Measurement and interpretation of electrokinetic phenomena", Pure Appl. Chem., 2005, vol. 77, No. 10, pp. 1753-1805.
Devergnas et al., A "Cortical potentials evoked by deep brain stimulation in the subthalamic area", Frontiers in System Neuroscience, May 13, 2011, vol. 5, Article 30, 2011, doi: 10.3389/fnsys.2011.00030.
Dijkstra, E. A. "Ultrasonic Distance Detection for a Closed-Loop Spinal Cord Stimulation System", Proceedings—19th International Conference—IEEE/EMBS Oct. 30-Nov. 2, 1997, Chicago, IL. 4 pgs.
Dillier, N. et al., "Measurement of the electrically evoked compound action potential via a neural response telemetry system", Ann. Otol. Rhinol. Laryngol., vol. 111, No. 5, May 2002, pp. 407-414.
Doi Ron et al., "Persistent Na+ Current Modifies Burst Discharge By Regulating Conditional Backpropagation of Dendritic Spikes", Journal of Neurophysiology 89, No. 1 (Jan. 1, 2003): 324- 337, doi:10.1152/jn.00729.2002.
England et al., "Increased Numbers of Sodium Channels Form Along Demyelinated Axons", Brain Research 548, No. 1-2 (May 10, 1991): 334-337.
European Search Report for European Application 12785619.3 Search Completed Oct. 13, 2014, dated Oct. 23, 2014, 7 pgs.
European Search Report for European Application 12785669.8 Search Completed Sep. 22, 2014, dated Sep. 29, 2014, 5 pgs.
European Search Report for European Application No. 15861444.6, Search completed Jul. 13, 2018, dated Jul. 23, 2018, 8 pgs.
Extended European Search Report for EP Application 12785483.4 completed Sep. 16, 2014, 7 pgs.

(56) References Cited

OTHER PUBLICATIONS

Extended European Search Report for European Application No. 11820923.8, report completed Dec. 9, 2013, dated Dec. 17, 2013, 6 pgs.
Extended European Search Report for European Application No. 13852669.4, Search completed Jun. 8, 2016, dated Jun. 22, 2016, 09 Pgs.
Extended European Search Report for European Application No. 14861553.7, Search completed Jun. 8, 2017, dated Jun. 19, 2017, 8 Pgs.
Extended European Search Report for European Application No. 14863597.2, Search completed Jun. 6, 2017, dated Jun. 13, 2017, 9 Pgs.
Extended European Search Report for European Application No. 15768956.3, Search completed Oct. 3, 2017, dated Oct. 10, 2017, 8 Pgs.
Extended European Search Report for European Application No. 15789515.2, Search completed Dec. 4, 2017, dated Jan. 30, 2018, 7 Pgs.
Extended European Search Report for European Application No. 16739680.3, Search completed Jun. 1, 2018, dated Jun. 12, 2018, 9 Pgs.
Extended European Search Report for European Application No. 16802237.4, Search completed Dec. 11, 2018, dated Dec. 19, 2018, 9 Pgs.
Extended European Search Report for European Application No. 16802238.2, Search completed Oct. 17, 2018, dated Oct. 24, 2018, 8 Pgs.
Extended European Search Report for European Application No. 17778477.4, report completed Nov. 12, 2019, dated Nov. 20, 2019, 7 pgs.
Extended European Search Report for European Application No. 17814341.8, report completed Dec. 12, 2019, report dated Jan. 2, 2020, 8 pgs.
Extended European Search Report for European Application No. 13853514.1, Search completed Jun. 8, 2016, dated Jun. 15, 2016, 07 Pgs.
Extended European Search Report in European Appln No. 18910394.8, dated October 215, 2021, 8 pages.
Extended European Search Report in European Appln No. 19793420.1, dated Dec. 17, 2021, 9 pages.
Extended European Search Report in European Appln No. 19875139.8, dated Jun. 15, 2022, 8 pages.
Extended European Search Report in European Appln No. 19899138.2, dated Aug. 3, 2022, 9 pages.
Fagius, J et al. "Sympathetic Reflex Latencies and Conduction Velocities in Normal Man", Journal of Neurological Sciences, 1980. Vol. 47, pp. 433-448.
Falowski et al., "Spinal Cord Stimulation: an update", Neurotherapeutics: The Journal of the American Society for Experimental NeuroTherapeutics 5, No. 1, Jan. 2008, pp. 86-99.
Fisher, "F-Waves—Physiology and Clinical Uses", TheScientific WorldJournal, (2007) 7, pp. 144-160.
Fitzpatrick et al., "A Nerve Cuff Design for the Selective Activation and Blocking of Myelinated Nerve Fibers", IEEE Engineering in Medicine and Biology Society, vol. 13, No. 2, 1991, pp. 906-907.
Franke et al., FELIX "An Online Spike Detection and Spike Classification Algorithm Capable of Instantaneous Resolution of Overlapping Spikes", Journal of Computational Neuroscience, 2010, vol. 29, No. 1-2, pp. 127-148.
French et al., "Information transmission at 500 bits/s by action potentials in a mechanosensory neuron of the cockroach", Neuroscience Letters, vol. 243, No. 1-3, Feb. 1, 1998, pp. 113-116.
Fuentes et al., "Spinal Cord Stimulation Restores Locomotion in Animal Models of Parkinson's Disease", Science, vol. 323, No. 5921, Mar. 20, 2009, pp. 1578-1582.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs., http://www.jneuroengrehab.com/content/10/1/2.
George et al., "Vagus nerve stimulation: a new tool for brain research and therapy", Biological Psychiatry 47, No. 4, Feb. 15, 2000, pp. 287-295.
Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, Doi: 10.1109/TBME.2003.816077.
Goodall et al., "Modeling Study of Activation and Propagation delays During Stimulation of Peripheral Nerve Fibres with a Tripolar Cuff Electrode", IEEE Transactions on Rehabilitation Engineering, Sep. 1995, vol. 3, No. 3, pp. 272-282.
Gorman et al., "ECAP Mapping of the Spinal Cord: Influence of Electrode Position on A13 Recruitment", (2012)., In 16th Annual Meeting. Presented at the North American Neuromodulation Society, Las Vegas, NV, 2 pgs.
Gorman et al., "Neural Recordings For Feedback Control of Spinal Cord Stimulation: Reduction of Paresthesia Variability.", 2013, In International Neuromodulation Society 11th World Congress, presented at the International Neuromodulation Society 11th World Congress, Berlin, Germany, 2 pgs.
Hallstrom et al., "Distribution of lumbar spinal evoked potentials and their correlation with stimulation-induced paresthesiae", Electroencephalography and Clinical Neurophysiology, Mar.- Apr. 1991, vol. 80, No. 2, pp. 126-139, doi: 10.1016/0168-5597(91)90150-V.
Harper et al., "Conduction Velocity is Related to Morphological Cell Type in Rat Dorsal Root Ganglion Neurones", J. Physiol, (1985), vol. 359, pp. 31-46.
He et al., "Perception threshold and electrode position for spinal cord stimulation", Pain, vol. 59, (1994), pp. 55-63.
Herreras, "Local Field Potentials: Myths and Misunderstandings", Frontiers in Neural Circuits, Dec. 15, 2016, vol. 10, Article 1101, 16 pgs., doi: 10.3389/fncir.2016.00101.
Holsheimer et al., "Optimum Electrode Geometry for Spinal Cord Stimulation: the Narrow Bipole and Tripole", Medical and Biological Engineering and Computing, 1997, vol. 35, No. 5, pp. 493-497.
Holsheimer et al., "Significance of the Spinal Cord Position in Spinal Cord Stimulation", Acta Neurochir (1995) [Suppl] 64, pp. 119-124.
Holsheimer et al., "Spinal Geometry and Paresthesia Coverage in Spinal Cord Stimulation", Neuromodulation, 1998, vol. 1, No. 3, pp. 129-136.
Howell et al., "Evaluation of Intradural Stimulation Efficiency and Selectivity in a Computational Model of Spinal Cord Stimulation", PLoS One, DOI:10.1371/journal.pone.0114938, Dec. 23, 2014.
Huff, Terry B. et al., "Real-Time CARS Imaging Reveals a Calpain-Dependent Pathway for Paranodal Myelin Retraction during High-Frequency Stimulation", PLoS One, vol. 6, Issue 3 (Mar. 3, 2011): e17176, 11 pgs., doi: 10.1371/journal.pone.0017176.
International Preliminary Report for International Application No. PCT/AU2017/050296, dated Oct. 9, 2018, 7 Pgs.
International Preliminary Report for International Application No. PCT/AU2017/050647, dated Dec. 25, 2018, 8 pgs.
International Preliminary Report on Patentability for International Application No. PCT/AU2012/001441, Report dated May 27, 2014, 10 pgs.
International Preliminary Report on Patentability for International Application No. PCT/AU2015/050135, Report dated Oct. 4, 2016, 13 pgs.
International Preliminary Report on Patentability for International Application No. PCT/AU2015/050215, Report dated Nov. 8, 2016, 4 pgs.
International Preliminary Report on Patentability for International Application No. PCT/AU2016/050263, Report dated Oct. 10, 2017, 9 pgs.
International Preliminary Report on Patentability for International Application No. PCT/AU2011/001127, Report dated Mar. 5, 2013, 9 pgs.

(56) References Cited

OTHER PUBLICATIONS

International Preliminary Report on Patentability for International Application No. PCT/AU2012/000511, Report dated Nov. 19, 2013, 6 pgs.
International Preliminary Report on Patentability for International Application No. PCT/AU2012/000512, Report dated Nov. 19, 2013, 8 pgs.
International Preliminary Report on Patentability for International Application No. PCT/AU2012/000513, Report dated Nov. 19, 2013, 11 pgs.
International Preliminary Report on Patentability for International Application No. PCT/AU2012/000515, Report dated Nov. 19, 2013, 5 pgs.
International Preliminary Report on Patentability for International Application No. PCT/AU2012/000516, Report dated Nov. 19, 2013, 9 pgs.
International Preliminary Report on Patentability for International Application No. PCT/AU2012/000517, Report dated Nov. 19, 2013, 6 pgs.
International Preliminary Report on Patentability for International Application No. PCT/AU2012/000518, Report dated Nov. 19, 2013, 11 pgs.
International Preliminary Report on Patentability for International Application No. PCT/AU2013/001279, Report dated May 12, 2015, 6 pgs.
International Preliminary Report on Patentability for International Application No. PCT/AU2013/001280, Report dated May 12, 2015, 6 pgs.
International Preliminary Report on Patentability for International Application No. PCT/AU2014/001049, Report dated May 17, 2016, 5 pgs.
International Preliminary Report on Patentability for International Application No. PCT/AU2014/050369, Report dated May 24, 2016, 8 pgs.
International Preliminary Report on Patentability for International Application No. PCT/AU2015/050422, Report dated Jan. 31, 2017, 8 pgs.
International Preliminary Report on Patentability for International Application No. PCT/AU2015/050724, Report dated May 23, 2017, 5 pgs.
International Preliminary Report on Patentability for International Application No. PCT/AU2015/050753, Report dated Jun. 13, 2017, 7 pgs.
International Preliminary Report on Patentability for International Application No. PCT/AU2015/050787, Report dated Jun. 13, 2017, 6 pgs.
International Preliminary Report on Patentability for International Application No. PCT/AU2016/050019, Report dated Jul. 25, 2017, 9 pgs.
International Preliminary Report on Patentability for International Application No. PCT/AU2018/050278, dated Sep. 29, 2020, 7 pgs.
International Preliminary Report on Patentability for International Application No. PCT/AU2019/050384, dated Oct. 27, 2020, 8 pgs.
International Search Report & Written Opinion for International Application No. PCT/AU2013/001280, Search Completed Jan. 16, 2014, dated Jan. 16, 2014, 8 Pgs.
International Search Report & Written Opinion for International Application PCT/AU2013/001279, Search Completed Jan. 9, 2014, dated Jan. 9, 2014, 9 Pgs.
International Search Report and Written Opinion for International Application No. PCT/AU2015/050724, Search completed May 9, 2016, dated May 9, 2016, 8 Pgs.
International Search Report and Written Opinion for International Application No. PCT/AU2011/001127, date completed Nov. 11, 2011, dated Nov. 15, 2011, 13 pgs.
International Search Report and Written Opinion for International Application No. PCT/AU2012/001441, International Filing Date Nov. 23, 2012, Search Completed Feb. 26, 2013, dated Feb. 26, 2013, 14 pgs.
International Search Report and Written Opinion for International Application No. PCT/AU2014/001049, Search completed Feb. 10, 2015, dated Feb. 10, 2015, 8 Pgs.
International Search Report and Written Opinion for International Application No. PCT/AU2014/050369, Search completed Feb. 20, 2015, dated Feb. 20, 2015, 14 Pgs.
International Search Report and Written Opinion for International Application No. PCT/AU2015/050135, Search completed Jun. 30, 2015, dated Jun. 30, 2015, 26 Pgs.
International Search Report and Written Opinion for International Application No. PCT/AU2015/050215, Search completed Jul. 30, 2015, dated Jul. 30, 2015, 8 Pgs.
International Search Report and Written Opinion for International Application No. PCT/AU2015/050422, Search completed Oct. 14, 2015, dated Oct. 14, 2015, 17 Pgs.
International Search Report and Written Opinion for International Application No. PCT/AU2015/050753, Search completed Feb. 10, 2016, dated Feb. 10, 2016, 10 Pgs.
International Search Report and Written Opinion for International Application No. PCT/AU2015/050787, Search completed Mar. 16, 2016, dated Mar. 16, 2016, 10 Pgs.
International Search Report and Written Opinion for International Application No. PCT/AU2016/050019, Search completed May 4, 2016, dated May 4, 2016, 16 Pgs.
International Search Report and Written Opinion for International Application No. PCT/AU2016/050263, Search completed Nov. 16, 2016, dated Nov. 16, 2016, 8 Pgs.
International Search Report and Written Opinion for International Application No. PCT/AU2016/050430, Search completed Aug. 16, 2016, dated Aug. 16, 2016, 10 Pgs.
International Search Report and Written Opinion for International Application No. PCT/AU2016/050431, Search completed Aug. 16, 2016, dated Aug. 16, 2016, 11 Pgs.
International Search Report and Written Opinion for International Application No. PCT/AU2016/050439, Search completed Jul. 15, 2016, dated Jul. 15, 2016, 8 Pgs.
International Search Report and Written Opinion for International Application No. PCT/AU2017/050296, Search completed Jul. 28, 2017, dated Jul. 28, 2017, 10 Pgs.
International Search Report and Written Opinion for International Application No. PCT/AU2017/050647, Search completed Sep. 29, 2017, dated Sep. 29, 2017, 13 Pgs.
International Search Report and Written Opinion for International Application No. PCT/AU2018/050278, Search completed Jun. 18, 2018, dated Jun. 18, 2018, 12 Pgs.
International Search Report and Written Opinion for International Application No. PCT/AU2019/050384, Search completed Jun. 25, 2019, dated Jun. 25, 2019, 15 Pgs.
International Search Report and Written Opinion for International Application No. PCT/AU2019/051385, Search completed Mar. 24, 2020, dated Mar. 24, 2020, 8 Pgs.
International Search Report for Australian Application 2011901829 Search Completed Feb. 6, 2012, dated Feb. 7, 2012, 3pgs.
International Search Report for International Application No. PCT/AU2012/000511, International Filing Date May 11, 2012, Search Completed May 17, 2012, dated May 18, 2012, 4 pgs.
International Search Report for International Application No. PCT/AU2012/000512, International Filing Date May 11, 2012, Search Completed Jul. 10, 2012, dated Jul. 11, 2012, 4 pgs.
International Search Report for International Application No. PCT/AU2012/000513, International Filing Date May 11, 2012, Search Completed May 29, 2012, dated May 30, 2012, 5 pgs.
International Search Report for International Application No. PCT/AU2012/000515, International Filing Date May 11, 2012, Search Completed May 21, 2012, dated Jun. 4, 2012, 5 pgs.
International Search Report for International Application No. PCT/AU2012/000516, International Filing Date May 11, 2012, Search Completed Jul. 11, 2012, dated Jul. 12, 2012, 8 pgs.
International Search Report for International Application No. PCT/AU2012/000517, International Filing Date May 11, 2012, Search Completed Jun. 4, 2012, dated Jun. 6, 2012, 3 pgs.

(56) References Cited

OTHER PUBLICATIONS

International Search Report for International Application No. PCT/AU2012/000518, International Filing Date May 11, 2012, Search Completed Jun. 8, 2012, dated Jun. 12, 2012, 4 pgs.
International Search Report for International Application No. PCT/AU2019/051151, International Filing Date Oct. 22, 2019, Search Completed Feb. 24, 2020, dated Feb. 24, 2020, 9 pgs.
International Search Report for International Application No. PCT/AU2019/051160, International Filing Date Oct. 23, 2019, Search Completed Jan. 28, 2020, dated Jan. 28, 2020, 13 pgs.
International Search Report for International Application No. PCT/AU2019/051163, International Filing Date Oct. 23, 2019, Search Completed Jan. 21, 2020, dated Jan. 31, 2020, 8 pgs.
International Search Report for International Application No. PCT/AU2019/051197, International Filing Date Oct. 30, 2019, Search Completed Jan. 21, 2020, dated Jan. 21, 2020, 15 pgs.
International Search Report for International Application No. PCT/AU2019/051210, International Filing Date Nov. 2, 2019, Search Completed Feb. 4, 2020, dated Feb. 4, 2020, 10 pgs.
International Type Search Report for International Application No. AU2015902393, Search completed May 16, 2016, dated May 16, 2016, 8 Pgs.
Islam et al., "Methods for artifact detection and removal from scalp EEG: A review," Neurophysiologie Clinique-Clinical Neurophysiology, Oct. 2016, 46(4): 287-305.
Jang et al, "Single Channel Signal Separation Using Time-Domain Basis Functions", IEEE Signal Processing Letters, Jun. 2003, vol. 10, No. 6, 13 pgs.
Jang et al., "A Maximum Likelihood Approach to Single-channel Source Separation", Journal of Machine Learning Research, Dec. 2003, vol. 4, pp. 1365-1392.
Japanese Office Action for Application No. 2017-546830, dated Feb. 20, 2020, 5 pages with English translation.
Japanese Office Action for Application No. 2017-553090, dated Mar. 16, 2020, 12 pages with English translation.
Japanese Office Action for Application No. 2018-552138, dated Mar. 1, 2021, 7 pages with English translation.
Japanese Office Action for Application No. 2018-513699, dated Jun. 8, 2020, 7 pages with English translation.
Jeffrey et al., "A reliable method for intracranial electrode implantation and chronic electrical stimulation in the mouse brain", BMC Neuroscience. Biomed Central. London, GB. vol. 14. No. 1, Aug. 6, 2013 (Aug. 6, 2013), pp. 1-8.
Jones et al., "Scaling of Electrode- Electrolyte Interface Model Parameters in Phosphate Buffered Saline", IEEE Transactions on Biomedical Circuits and Systems, 2015, vol. 9, No. 3, pp. 441-448, DOI:10.1109/TBCAS.2014.4223759.
Kent et al., "Instrumentation to Record Evoked Potentials for Closed-Loop Control of Deep Brain Stimulation", Conf. Proc. IEEE Eng. Med Biol. Sol, Aug. 2012, pp. 6777-6780, doi: 10.1109/IEMBS.20113.6091671.
Kent et al., AR "Recording evoked potentials during deep brain stimulation: development and validation of instrumentation to suppress the stimulus artefact", J Neural Eng., Jun. 2012, vol. 9, No. 3, 036004, doi: 10.1088/17 41-2560/9/3/036004.
Kent, "Characterization of Evoked Potentials During Deep Brain Stimulation in the Thalamus", Dissertation, Duke University. Retrieved from https://hdl.handle.net/10161/8195, 2013. https://dukespace.lib.duke.edu/dspace/handle/10161/8195.
Kim et al., "A Wavelet-Based Method for Action Potential Detection From Extracellular Neural Signal Recording With Low Signal-to-Noise Ratio", IEEE Transactions on Biomedical Engineering, Aug. 2003, vol. 50. No. 8, pp. 999-1011.
Kim et al., "Cell Type-specific Changes of the Membrane Properties of Peripherally-axotomized Dorsal Root Ganglion Neurons in a Rat Model of Neuropathic Pain", Neuroscience, vol. 86, No. 1, May 21, 1998, pp. 301-309, doi: 10.1016/S0306-4522(98)00022-0.
Kopelman et al., "Attempted Reversible Sympathetic Ganglion Block by An Implantable Neurostimulator", Interactive Cardiovascular and Thoracic Surgery, Feb. 7, 2012, vol. 14, Issue 5, p. 605-609, doi: 10.1093/icvts/ivr137.
Krames et al., "Neuromodulation", 1st Edition, Academic Press, 2009, pp. 540-541.
Krarup, Christian "Compound sensory action potential in normal and pathological human nerves", Muscle & Nerve, Apr. 2004, vol. 29, No. 4, pp. 465-483.
Krishnan et al., "Excitability Differences in Lower-Limb Motor Axons During and After Ischemia", Muscle & nerve, vol. 31, No. 2 (2005), pp. 205-213.
Kumar et al., "Deep Brain Stimulation for Intractable Pain: a 15-year Experience", Neurosurgery, Issue 40, No. 4, Apr. 1997, pp. 736-747.
Kumar et al., "Double-blind evaluation of subthalamic nucleus deep brain stimulation in advanced Parkinson's disease", by the American Academy of Neurology, 51, No. 3, Sep. 1, 1998, pp. 850-855.
Kumar et al., "Globus Pallidus Deep Brain Stimulation for Generalized Dystonia: Clinical and PET Investigation", Sep. 11, 1999, vol. 53, No. 4, pp. 871-874, doi:10.1212/WNL.53.4.871.
Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.
Laird-Wah, "Improving Spinal Cord Stimulation: Model-Based Approaches to Evoked Response Telemetry", UNSWThesis, Aug. 2015, 279 pgs.
Lempka, Scott "The Electrode-Tissue Interface During Recording and Stimulation in the Central Nervous System", Thesis, 155 pgs., published May 2010.
Levy et al., "Incidence and Avoidance of Neurologic Complications with Paddle Type Spinal Cord Stimulation Leads", Neuromodulation, Sep. 2011, vol. 14, No. 15, pp. 412-422, https://doi.org/10.1111/j.1525-1403.2011.00395.x.
Li, S. et al., "Resonant antidromic cortical circuit activation as a consequence of high-frequency subthalamic deep-brain stimulation", J Neurophysiol. Dec. 2007; 98(6): 3525-37. First published Oct. 10, 2007. doi: 10.1152/jn.00808.2007.
Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.
Macefield, "Spontaneous and Evoked Ectopic Discharges Recorded from Single Human Axons", Muscle & Nerve 21, No. 4, Apr. 1998, pp. 461-468.
Mah Nam et al., "Measurement of the current-distance relationship using a novel refractory interaction technique", J. Neural Eng. 6(2): 036005, published May 20, 2009, 22 pgs.
Mannan et al., "Identification and Removal of Physiological Artifacts From Electroencephalogram Signals: A Review", IEEE Access, May 31, 2018, vol. 6, pp. 30630-30652, https://doi.org/10.1109/ACCESS.2018.2842082.
Markandey, Vishal "ECG Implementation on the TMS320C5515 DSP Medical Development Kit (MOK)", Texas Instruments Application Report Jun. 2010, 35 pgs.
Massachusetts Institute of Technology, The Compound Action Potential of the Frog Sciatic Nerve, Quantitative Physiology: Cells and Tissues. Fall, 1999, Retrieved from http://umech.mit.edu/freeman/6.021J/2001/lab.pdf on May 22, 2012.
Matzner et al., "Na+ Conductance and the Threshold for Repetitive Neuronal Firing", Brain Research 597, No. 1 (Nov. 27, 1992): 92-98, doi: 10.1016/0006-8993(92)91509-D.
McGill, Kevin et al., "On the Nature and Elimination of Stimulus Artifact in Nerve Signals Evoked and Recorded Using Surface Electrodes", IEEE Transactions on Biomedical Engineering, vol. BME- 29, No. 2, Feb. 1982, pp. 129-137.
Medtronic, RestoreSensor Neurostimulator, Retrieved from: http://web.archive.org/web/20150328092923/http://professional.medtronic.com:80/pt/neuro/scs/prod/restore-sensor/featuresspecifications/index.htm, Capture Date Jul. 9, 2012, Printed on May 11, 2017.
Medtronic, Spinal Cord Stimulation, RestoreSensor Neurostimulator, Features and Specification: Specification, Printed Jun. 16, 2014, 2 pgs.

(56) References Cited

OTHER PUBLICATIONS

Medtronic, Spinal Cord Stimulation, RestoreSensor Neurostimulator, Features and Specification: Summary Printed Jun. 16, 2014, 1 pg.

Melzack et al., "Pain mechanisms: a new theory", Science, New York, New York, vol. 150, No. 3699, Nov. 19, 1965, pp. 971-979.

Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445.

Misawa et al., "Neuropathic Pain Is Associated with Increased Nodal Persistent Na(+) Currents in Human Diabetic Neuropathy", Journal of the Peripheral Nervous System: JPNS, 14, No. 4 (Dec. 2009): 279-284.

Niazy et al., "Removal of FMRI environment artifacts from EEG data using optimal basis sets", NeuroImage, 2005, vol. 28, pp. 720-737, available online Sep. 16, 2005, doi:10.1016/j.neuroimage.2005.06.0607.

Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi:10.1016/0304-3959(84)90013-7.

North et al., "Prognostic value of psychological testing in patients undergoing spinal cord stimulation: a prospective study", Neurosurgery, Aug. 1, 1996, vol. 39, Issue 2, pp. 301-311. https://doi.org/10.1097/00006123-199608000-00013.

Oakley et al., "Spinal Cord Stimulation: Mechanisms of Action", Spine 27, No. 22, Nov. 15, 2002, pp. 2574-2583.

Oakley et al., "Transverse Tripolar Spinal Cord Stimulation: Results of an International Multicenter Study", Neuromodulation, vol. 9, No. 3, 2006, pp. 192-203.

Obradovic et al., "Effect of pressure on the spinal cord during spinal cord stimulation in an animal model", Poster, 18th Annual Meeting of the North American Neuromodulation Society, Dec. 11-14, 2014, Las Vegas.

Office Action for Chinese Patent Application No. 201680020725.4, dated Mar. 16, 2020, 8 pgs.

Oh et al., "Long-term hardware-related complications of deep brain stimulation", Neurosurgery, vol. 50, No. 6, Jun. 2002, pp. 1268-1274, discussion pp. 1274-1276.

Olin et al., "Postural Changes in Spinal Cord Stimulation Perceptual Thresholds", Neuromodulation, vol. 1, No. 4, 1998, pp. 171-175.

Opsommer, E. et al. "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.

Orstavik et al., "Pathological C-fibres in patients with a chronic painful condition", Brain (2003), 126, 567-578.

Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.

Parker et al., "Closing the Loop in Neuromodulation Therapies: Spinal Cord Evoked Compound Action Potentials During Stimulation for Pain Management (230).", 2011, In 15th Annual Meeting, North American Neuromodulation Society (p. 48). Presented at the North American Neuromodulation Society, Las Vegas.

Parker et al., "Compound Action Potentials Recorded in the Human Spinal Cord During Neurostimulation for Pain Relief", Pain, vol. 153, 2012, pp. 593-601.

Parker et al., "Electrically Evoked Compound Action Potentials Recorded From the Sheep Spinal Cord", Neuromodulation, vol. 16, 2013, pp. 295-303.

Partial European Search Report for European Application No. 16775966.1, Search completed Oct. 26, 2018, dated Nov. 6, 2018, 11 Pgs.

Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.

Peterson et al., "Stimulation artifact rejection in closed-loop, distributed neural interfaces", ESSCI RC, 42nd European Solid-State Circuits Conference, Lausanne, 2016, pp. 233-235.

Rattay, "Analysis of Models for External Stimulation of Axons", IEEE Transactions on Biomedical Engineering, vol. BME-33, No. 10, Oct. 1986, pp. 974-977.

Richter et al., "EMG and SSEP Monitoring During Cervical Spinal Cord Stimulation", Journal of Neurosurgical Review 2011, Southern Academic Press, 1(S1), 2011, pp. 61-63.

Ridder et al., "Burst Spinal Cord Stimulation for Limb and Back Pain", World Neurosurgery, 2013, 9 pgs.

Rijkhoff et al., "Acute Animal Studies on the Use of Anodal Block to Reduce Urethral Resistance in Sacral Root Stimulation", IEEE Transactions on Rehabilitation Engineering, 1994, vol. 2, No. 2, pp. 92-99.

Rijkhoff et al., "Orderly Recruitment of Motoneurons in an Acute Rabbit Model", Annual International Conference of the IEEE Engineering in Medicine and Biology Society, 1998, vol. 20, No. 5, pp. 2564-2565.

Ross et al., "Improving Patient Experience with Spinal Cord Stimulation: Implications of Position- Related Changes in Neurostimulation", Neuromodulation 2011; e-pub ahead of print. DOI:10.1111/j.1525-1403.2011.00407.x 6 pages.

Roy et al., "Effects of Electrode Location on Myoelectric Conduction Velocity and Median Frequency Estimates", J. Appl. Physiol. 61 (4), 1986, pp. 1510-1517.

Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.

Schmidt et al., "Gating of tactile input from the hand", Exp Brain Res, 1990, 79, pp. 97-102.

Scott et al., "Compact Nonlinear Model of an Implantable Electrode Array for Spinal Cord Stimulation (SCS)", IEEE Transactions on Biomedical Circuits and Systems, 2014, vol. 8, No. 3, pp. 382-390.

Siegfried et al., "Bilateral Chronic Electrostimulation of Ventroposterolateral Pallidum: A New Therapeutic Approach for Alleviating All Parkinsonian Symptoms", Issue: vol. 35(6), Dec. 1994, p. 1126-1130; Copyright: Copyright by the Congress of Neurological Surgeons; Publication Type: [Technique and Application, ISSN: 0148-396X; Accession: 00006123-199412000-00016; Keywords: Chronic deep brain stimulation, Pallidum, Parkinson's disease, Stereotactic operation.

Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.

Siegfried et al., "Intracerebral Electrode Implantation System", Journal of Neurosurgery, vol. 59, No. 2, Aug. 1983, pp. 356-359.

Srinivasan, S "Electrode/Electrolyte Interfaces: Structure and Kinetics of Charge Transfer", Fuel Cells, 2006, Chapter 2, 67 Pages.

Stanslaski et al., "Design and Validation of a Fully Implantable, Chronic, Closed-Loop Neuromodulation Device with Concurrent Sensing and Stimulation", IEEE Transactions on Neural Systems and Rehabilitation Engineering, Jul. 2012, Date of Publication: Jan. 23, 2012, vol. 20, No. 4, pp. 410-421, Doi: 10.1109/TNSRE.2012.2183617.

Struijk et al., "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.

Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.

Struijk, "The Extracellular Potential of a Myelinated Nerve Fiber in an Unbounded Medium and in Nerve Cuff Models", Biophysical Journal vol. 72 Jun. 1997 2457-2469.

Sufka et al., "Gate Control Theory Reconsidered", Brain and Mind, 3, No. 2, 2002, pp. 277-290.

Takahashi et al., "Classification of neuronal activities from tetrode recordings using independent component analysis", Neurocomputing, (2002), vol. 49, Issues 1-4, pp. 289-298.

(56) References Cited

OTHER PUBLICATIONS

Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.

Tasker, "Deep Brain Stimulation is Preferable to Thalamotomy for Tremor Suppression", Surgical Neurology, 49, No. 2, 1998, pp. 145-153.

Taylor et al., "Spinal Cord Stimulation for Chronic Back and Leg Pain and Failed Back Surgery Syndrome: A Systematic Review and Analysis of Prognostic Factors", Spine, vol. 30, No. 1, 2004, pp. 152-160.

Texas Instruments, "Precision, Low Power Instrumentation Amplifiers", Texas Instruments SBOS051B Oct. 1995, Revised Feb. 2005, 20 pgs.

Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.

Tronnier et al., "Magnetic Resonance Imaging with Implanted Neurostimulators: An In Vitro and In Vivo Study", Jan. 1999, Neurosurgery, vol. 44(1), pp. 118-125 (Year: 1999).

Tscherter et al., "Spatiotemporal Characterization of Rhythmic Activity in Rat Spinal Cord Slice Cultures", European Journal of Neuroscience 14, No. 2 (2001), pp. 179-190.

Van Den Berg et al., "Nerve fiber size-related block of action currents by phenytoin in mammalian nerve", Epilepsia, Nov. 1994, 35(6), pp. 1279-1288.

Villavicencio, Alan T. "Laminectomy versus Percutaneous Electrode Placement for Spinal Cord Stimulation," Neurosurgery, vol. 46 (2), Feb. 2000, pp. 399-405.

Vleggeert et al., LANKAMP "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.

Woessner, "Blocking Out the Pain, Electric Nerve Block Treatments for Sciatic Neuritis", Retrieved from: http://www.practicalpainmanagement.com/pain/spine/radiculopathy/blocking-out- pain, Last updated Jan. 10, 2012.

Wolter et al., "Effects of sub-perception threshold spinal cord stimulation in neuropathic pain: A randomized controlled double-blind crossover study", European Federation of International Association for the Study of Pain Chapters, 2012, pp. 648-655.

Written Opinion for International Application No. PCT/AU2012/000511, International Filing Date May 11, 2012, Search Completed May 17, 2012, dated May 18, 2012, 5 pgs.

Written Opinion for International Application No. PCT/AU2012/000512, International Filing Date May 11, 2012, Search Completed Jul. 10, 2012, dated Jul. 11, 2012, 7 pgs.

Written Opinion for International Application No. PCT/AU2012/000513, International Filing Date May 11, 2012, Search Completed May 29, 2012, dated May 30, 2012, 10 pgs.

Written Opinion for International Application No. PCT/AU2012/000515, International Filing Date May 11, 2012, Search Completed May 21, 2012, dated Jun. 4, 2012, 4 pgs.

Written Opinion for International Application No. PCT/AU2012/000516, International Filing Date May 11, 2012, Search Completed Jul. 11, 2012, dated Jul. 12, 2012, 8 pgs.

Written Opinion for International Application No. PCT/AU2012/000517, International Filing Date May 11, 2012, Search Completed Jun. 4, 2012, dated Jun. 6, 2012, 5 pgs.

Written Opinion for International Application No. PCT/AU2012/000518, International Filing Date May 11, 2012, Search Completed Jun. 8, 2012, dated Jun. 12, 2012, 10 pgs.

Wu et al., "Changes in A13 Non-nociceptive Primary Sensory Neurons in a Rat Model of Osteoarthritis Pain", Molecular Pain 6, No. 1 (Jul. 1, 2010): 37, doi:10.1186/1744-8069-6-37.

Wulfhorst et al., Textile Technology, Carl Hanser Verlag Munich 2006.

Xie et al., "Functional Changes in Dorsal Root Ganglion Cells after Chronic Nerve Constriction in the Rat", Journal of Neurophysiology, vol. 73, No. 5 (May 1, 1995): 1811-1820.

Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.

Yamada et al., "Extraction and Analysis of the Single Motor Unit Fwave of the Median Nerve", EMG Methods for Evaluating Muscle and Nerve Function, InTech, 2012, 15 pgs.

Yearwood, T. L. "Pulse Width Programming in Spinal Cord Stimulation: a Clinical Study", Pain Physician. 2010. Vol. 13, pp. 321-335.

Yingling et al., "Use of Antidromic Evoked Potentials in Placement of Dorsal Cord Disc Electrodes", Applied Neurophysiology, 1986, vol. 49, pp. 36-41.

Yuan, S. et al. "Recording monophasic action potentials using a platinum-electrode ablation catheter", Europace. Oct. 2000; 2(4):312-319.

Zhang et al., "Automatic Artifact Removal from Electroencephalogram Data Based on a Priori Artifact Information", BioMed Research International, Aug. 25, 2015, Article ID 720450, 8 pgs., DOI: https://doi.org/10.1155/2015/720450.

Metal electrode
in uniform field

Flow between metal
electrodes in ionic solution

Segmented
sense electrode

Segmented drive electrode

METHOD AND APPARATUS FOR ESTIMATING NEURAL RECRUITMENT

CROSS-REFERENCE TO RELATED APPLICATIONS

This application is a continuation of U.S. patent application Ser. No. 15/928,040 filed Mar. 21, 2018, which is a continuation of U.S. patent application Ser. No. 14/117,152 filed Nov. 12, 2013 and issued as U.S. Pat. No. 9,974,455 on May 22, 2018, which is the National Stage of International Application No. PCT/AU2012/000517 filed May 11, 2012, which claims the benefit of Australian Provisional Patent Application No. 2011901827 filed May 13, 2011 and Australian Provisional Patent Application No. 2011901817 filed May 13, 2011, all of which are incorporated herein by reference.

TECHNICAL FIELD

The present invention relates to measuring a neural response to a stimulus, and in particular relates to measurement of a compound action potential by using one or more electrodes implanted proximal to the neural pathway, in order to estimate neural recruitment resulting from an applied stimuli.

BACKGROUND OF THE INVENTION

There are a range of situations in which it is desirable to apply neural stimuli in order to give rise to a compound action potential (CAP). For example, neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord. Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and generation of propagating action potentials. The fibres being stimulated in this way inhibit the transmission of pain from that segment in the spinal cord to the brain. To sustain the pain relief effects, stimuli are applied substantially continuously, for example at 100 Hz.

While the clinical effect of spinal cord stimulation (SCS) is well established, the precise mechanisms involved are poorly understood. The DC is the target of the electrical stimulation, as it contains the afferent Aβ fibres of interest. Aβ fibres mediate sensations of touch, vibration and pressure from the skin, and are thickly myelinated mechanoreceptors that respond to non-noxious stimuli. The prevailing view is that SCS stimulates only a small number of Aβ fibres in the DC. The pain relief mechanisms of SCS are thought to include evoked antidromic activity of Aβ fibres having an inhibitory effect, and evoked orthodromic activity of Aβ fibres playing a role in pain suppression. It is also thought that SCS recruits Aβ nerve fibres primarily in the DC, with antidromic propagation of the evoked response from the DC into the dorsal horn thought to synapse to wide dynamic range neurons in an inhibitory manner.

Neuromodulation may also be used to stimulate efferent fibres, for example to induce motor functions. In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

The action potentials generated among a large number of fibres sum to form a compound action potential (CAP). The CAP is the sum of responses from a large number of single fibre action potentials. The CAP recorded is the result of a large number of different fibres depolarising.

The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak potential P1, then a negative peak N1, followed by a second positive peak P2. This is caused by the region of activation passing the recording electrode as the action potentials propagate along the individual fibres. An observed CAP signal will typically have a maximum amplitude in the range of microvolts, whereas a stimulus applied to evoke the CAP is typically several volts.

To resolve a 10 µV SCP with 1 µV resolution in the presence of an input 5V stimulus, for example, requires an amplifier with a dynamic range of 134 dB, which is impractical in implant systems. As the neural response can be contemporaneous with the stimulus and/or the stimulus artefact, CAP measurements are difficult to obtain. This is particularly so for pain relief where patients typically obtain best effects with a pulse width in the range of 100-500 µs which ensures much of the neural response occurs while the stimulus is still ongoing, making measurement of the neural response effectively impossible.

For effective and comfortable operation, it is necessary to maintain stimuli amplitude or delivered charge above a recruitment threshold, below which a stimulus will fail to recruit any neural response. It is also necessary to apply stimuli which are below a comfort threshold, above which uncomfortable or painful percepts arise due to increasing recruitment of Aδ fibres which are thinly myelinated sensory nerve fibres associated with acute pain, cold and pressure sensation. In almost all neuromodulation applications, a single class of fibre response is desired, but the stimulus waveforms employed can recruit other classes of fibres which cause unwanted side effects, such as muscle contraction if motor fibres are recruited. The task of maintaining appropriate stimulus amplitude is made more difficult by electrode migration and/or postural changes of the implant recipient, either of which can significantly alter the neural recruitment arising from a given stimulus, depending on whether the stimulus is applied before or after the change in electrode position or user posture. Postural changes alone can cause a comfortable and effective stimulus regime to become either ineffectual or painful.

Another control problem, faced by neuromodulation systems of all types, is achieving neural recruitment at a sufficient level required for therapeutic effect, but at minimal expenditure of energy. The power consumption of the stimulation paradigm has a direct effect on battery requirements which in turn affects the device's physical size and lifetime. For rechargeable systems, increased power consumption results in more frequent charging and, given that batteries only permit a limited number of charging cycles, ultimately this reduces the lifetime of the device.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect the present invention provides a method of estimating neural recruitment arising from a selected neural stimulus, the method comprising:
 applying the selected neural stimulus;
 after the selected neural stimulus, applying a probe stimulus having a short pulse width;
 measuring a remnant neural response evoked by the probe stimulus; and
 from the remnant neural response, estimating neural recruitment caused by the selected neural stimulus.

According to a second aspect the present invention provides an implantable device for estimating neural recruitment arising from a selected neural stimulus, the device comprising:
 a plurality of electrodes including one or more nominal stimulus electrodes and one or more nominal sense electrodes;
 a stimulus source for providing stimuli to be delivered from the one or more stimulus electrodes to neural tissue;
 measurement circuitry for obtaining a measurement of a neural signal sensed at the one or more sense electrodes; and
 a control unit configured to control application of a selected stimulus to neural tissue using the stimulus electrodes; the control unit further configured to, after the selected neural stimulus, apply a probe stimulus having a short pulse width; the control unit further configured to measure a remnant neural response evoked by the probe stimulus; and the control unit further configured to estimate from the remnant neural response a neural recruitment caused by the selected neural stimulus.

The present invention thus provides for probing of an un-recruited fibre population which was not recruited by the selected stimulus, by reference to which an understanding of the population recruited by the selected stimulus can be obtained.

Embodiments of the invention may be particularly beneficial in providing for estimation of neural recruitment effected by a selected stimulus having a long pulse width, for example in the range of 100-500 μs, in relation to which it is not possible to directly measure a neural response due to temporal overlap of the stimulus and response.

In preferred embodiments, the probe stimulus is applied quickly after the selected stimulus, within the refractory period of the fibres recruited by the selected stimulus.

In some embodiments, a second probe stimulus is applied after the refractory period of fibres recruited by either the selected stimulus or the probe stimulus, and a second measure of evoked neural response is obtained as caused by the second probe stimulus. In such embodiments, the neural recruitment arising from the selected neural stimulus may be estimated by comparing the remnant neural response to the second measure.

Additionally or alternatively, some embodiments may comprise:
 a) applying the probe stimulus at a time t after conclusion of the selected stimulus;
 b) obtaining a measure of a remnant neural response arising from the probe stimulus;
 c) changing t; and
 d) repeating (a), (b) and (c) to determine variations in the remnant neural response measure, with varying t.

For example, with increasing t an increase in the remnant neural response may indicate the refractory period of the fibre population recruited by the selected stimulus.

In embodiments of the invention in which an estimate of refractory period is obtained, the refractory period may be monitored over time in order to diagnose onset or progression of a disease.

According to another aspect the present invention provides a computer program product comprising computer program code means to make a computer execute a procedure for estimating neural recruitment arising from a selected neural stimulus, the computer program product comprising computer program code means for carrying out the method of the first aspect.

According to a first aspect the present invention provides a method for measuring a neural response to a stimulus, the method comprising:
 settling measurement circuitry prior to a stimulus, by connecting a sense electrode to the measurement circuitry to allow the measurement circuitry to settle towards a bio-electrically defined steady state;
 recovering charge on stimulus electrodes by short circuiting the stimulus electrodes to each other;
 applying an electrical stimulus from the stimulus electrodes to neural tissue, while keeping the sense electrode disconnected from the measurement circuitry;
 imposing a delay during which the stimulus electrodes are open circuited and the sense electrode is disconnected from the measurement circuitry and from the stimulus electrodes; and
 after the delay, measuring a neural response signal present at the sense electrode by connecting the sense electrode to the measurement circuitry.

According to a second aspect the present invention provides an implantable device for measuring a neural response to a stimulus, the device comprising:
 a plurality of electrodes including one or more nominal stimulus electrodes and one or more nominal sense electrodes;
 a stimulus source for providing a stimulus to be delivered from the one or more stimulus electrodes to neural tissue;
 measurement circuitry for amplifying a neural signal sensed at the one or more sense electrodes; and
 a control unit configured to control application of a stimulus to the neural tissue and measurement of an evoked neural response, the control unit configured to settle the measurement circuitry prior to a stimulus by connecting the or each sense electrode to the measurement circuitry to allow the measurement circuitry to settle towards a bioelectrically defined steady state, the control unit further configured to recover charge on the stimulus electrodes by short circuiting the stimulus electrodes to each other, the control unit further configured to cause the stimulus source to apply an electrical stimulus from the stimulus electrodes to neural tissue while keeping the or each sense electrode disconnected from the measurement circuitry, the control unit further configured to impose a delay during which the stimulus electrodes are open circuited and the sense electrode is disconnected from the measurement circuitry and from the stimulus electrodes, and the control unit further configured to measure a neural response signal present at the sense electrode by connecting the or each sense electrode to the measurement circuitry after the delay.

It is to be understood herein that open circuiting of an electrode involves ensuring that the electrode is disconnected from other electrodes, the stimulus source, the measurement circuitry and from voltage rails. Ensuring that the sense electrode is disconnected from the stimulus electrodes during the delay period avoids charge transfer onto the sense electrode(s) and associated artefact. The present invention recognizes that connecting the sense electrodes to the stimulus electrodes during a post-stimulus delay period can undesirably give rise to such charge transfer and associated artefact, particularly if the delay is short relative to the time constant of the stimulus electrodes, the latter typically being around 100 µs. The sense electrode is preferably open circuited during the post-stimulus delay so as to be disconnected from all other electrodes of the array, to prevent such charge transfer to the sense electrode from other non-stimulus electrodes.

The present invention recognizes that it is beneficial to provide for pre-stimulus settling of the measurement circuitry towards a bio-electrically defined steady state. This ensures that charge recovery occurs in the settling stage prior to the stimulus and not during or immediately after the stimulus and thus does not give rise to artefact during or immediately after the stimulus. Where repeated measurement cycles are undertaken, the present invention further permits the measurement amplifier to accumulate a bias point over multiple cycles rather than re-setting the bias point each cycle. The settle period is preferably sufficiently long to permit the electrodes and circuitry to reach an equilibrium, and for example the settle period may be around 1 ms or greater, as permitted by a stimulus rate. For example if therapeutic stimuli are applied to a dorsal column at about 100 Hz and do not give rise to a slow neural response, then after the approximately 2 ms duration of an evoked fast response up to about 8 ms would be available for the settling period. However, this is generally longer than required and the settling period may be substantially less than 8 ms.

The delay may be in the range of substantially zero to 1 ms, and for example may be about 0.3 ms. Such embodiments permit onset of the neural response to be observed, this typically occurring about 0.3 ms after the stimulus for an electrode 3 cm away from the stimulus site. In embodiments in which an amplifier of the measurement circuitry has a very high dynamic range, the delay may be set to a smaller value. The delay is preferably set to a value which ensures the measurement amplifier is not saturated and therefore performs linearly at all times when connected without experiencing clipping, and for example a feedback loop may be implemented to determine a suitable delay which avoids amplifier saturation for a given stimulus.

In preferred embodiments of the invention, the signal from the or each sense electrode is passed to a sample-and-hold circuit at the input of a measurement amplifier. In such embodiments measurements of a single evoked response may be obtained from a plurality of sense electrodes, even if the measurement circuitry of each electrode is connected to the control unit only by a two wire bus or the like, as is commonly required in implanted electrode arrays.

Additionally or alternatively, a buffer or follower amplifier is preferably provided in some embodiments, between the sense electrode and the measurement amplifier. The buffer is preferably connected to the sense electrode without interposed switches, so that the high reverse impedance of the buffer effectively prevents switching transients from being conveyed to the sense electrode, thereby avoiding artefact which may arise upon the sense electrode if subjected to such transients. The buffer amplifier is also preferably configured to give current gain to drive a storage capacitor of a sample and hold circuit. A series capacitor may be interposed between the sense electrode and the buffer to avoid DC transfer with the tissue.

In preferred embodiments of the invention, the stimulus and sense electrodes are selected from an implanted electrode array. The electrode array may for example comprise a linear array of electrodes arranged in a single column along the array. Alternatively the electrode array may comprise a two dimensional array having two or more columns of electrodes arranged along the array. Preferably, each electrode of the electrode array is provided with an associated measurement amplifier, to avoid the need to switch the sense electrode(s) to a shared measurement amplifier, as such switching can add to measurement artefact. Providing a dedicated measurement amplifier for each sense electrode is further advantageous in permitting recordings to be obtained from multiple sense electrodes simultaneously.

The measurement may be a single-ended measurement obtained by passing a signal from a single sense electrode to a single-ended amplifier. Alternatively, the measurement may be a differential measurement obtained by passing signals from two sense electrodes to a differential amplifier.

While recovering charge by short circuiting the stimulus electrodes together, it may in some embodiments be advantageous to disconnect the sense electrode from the measurement circuitry, for example by setting a sample-and-hold circuit to "hold".

Embodiments of the invention may prove beneficial in obtaining a CAP measurement which has lower dynamic range and simpler morphology as compared to systems more susceptible to artefact. Such embodiments of the present invention may thus reduce the dynamic range requirements of implanted amplifiers, and may avoid or reduce the complexity of signal processing systems for feature extraction, simplifying and miniaturizing an implanted integrated circuit. Such embodiments may thus be particularly applicable for an automated implanted evoked response feedback system for stimulus control. Thus, in a further aspect, the present invention provides a method for feedback control of a neural stimulus, the method comprising an implanted control unit obtaining a CAP measurement in accordance with the method of the first aspect, and the implanted control unit using the obtained CAP measurement to control the delivery of subsequent neural stimuli by the implant.

In some embodiments of the invention, an averaged CAP measurement may be obtained by (i) delivering a first biphasic stimulus which starts with a pulse of a first polarity and then delivers a pulse of a second polarity opposite to the first polarity, and obtaining a first measurement of a CAP evoked by the first stimulus; (ii) delivering a second biphasic stimulus which starts with a pulse of the second polarity and then delivers a pulse of the first polarity, and obtaining a second measurement of a CAP evoked by the second stimulus; and (iii) taking an average of the first measurement and the second measurement to obtain an averaged measurement. Such embodiments exploit the observation that artefact polarity usually reflects the stimulus polarity, whereas the CAP polarity is independent of the stimulus polarity and is instead determined by the anatomy and physiology of the spinal cord membrane, so that averaging the first and second measurements will tend to selectively cancel out artefact. Further noting that an "anodic first" biphasic stimulus usually has a lower stimulus threshold for neural recruitment than a "cathodic first" biphasic stimulus, the averaged measurement may have a morphology of either (i) a typical CAP of half amplitude if only the anodic-first stimulus exceeds the stimulus threshold; (ii) the average of two CAPs of different amplitude if both stimuli exceed the stimulus threshold but the cathodic first stimulus does not cause saturation recruitment; or (iii) a typical CAP if both stimuli exceed saturation recruitment. Some embodiments may therefore obtain a curve of the averaged measurement vs. stimulus amplitude in order to obtain information regarding the recruitment effected by each stimulus, and such information may be used for feedback control by the implant.

In some embodiments, the method of the present invention may be applied contemporaneously with administration of a drug, in order to gauge efficacy of drug delivery. For example, the implant may comprise or be operatively connected to a drug reservoir and drug delivery pump, with the pump being controlled by feedback based on CAP measurements.

According to another aspect the present invention provides a computer program product comprising computer program code means to make an implanted processor execute a procedure for measuring a neural response to a stimulus, the computer program product comprising computer program code means for carrying out the method of the first aspect.

The present invention recognises that when considering spinal cord stimulation, obtaining information about the activity within the spinal segment where stimulation is occurring is highly desirable. Observing the activity and extent of propagation both above (rostrally of) and below (caudally of) the level of stimulation is also highly desirable. The present invention recognises that in order to record the evoked activity within the same spinal segment as the stimulus requires an evoked potential recording system which is capable of recording an SCP within approximately 3 cm of its source, i.e. within approximately 0.3 ms of the stimulus.

In preferred embodiments the stimulus comprises a biphasic pulse, and the stimulus electrodes have no capacitors. In contrast to a monophasic pulse and capacitor arrangement, such embodiments permit the stimulus electrode current to be interrupted, or forced to zero, at those times where it would interfere with measurement. Omitting capacitors is also desirable in order to minimise the size of the implanted device.

BRIEF DESCRIPTION OF THE DRAWINGS

An example of the invention will now be described with reference to the accompanying drawings, in which:

FIG. 13A illustrates the "anodic first" and "cathodic first" CAP responses induced by the method of FIG. 12, while

DESCRIPTION OF THE PREFERRED EMBODIMENTS

Figure 1:
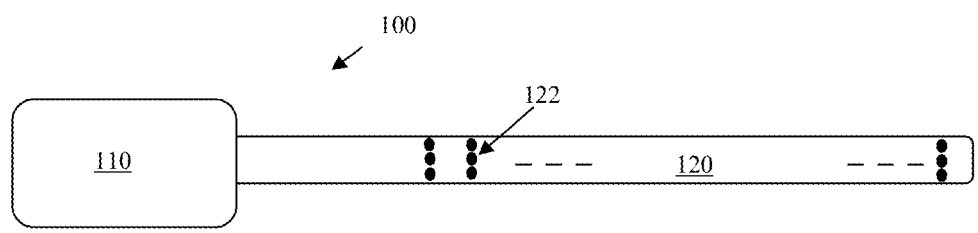
FIG. 1 illustrates an implantable device suitable for implementing the present invention.

FIG. 1 illustrates an implantable device 100 suitable for implementing the present invention. Device 100 comprises an implanted control unit 110, which controls application of neural stimuli, and controls a measurement process for obtaining a measurement of a neural response evoked by the stimuli from each of a plurality of electrodes. Device 100 further comprises an electrode array 120 consisting of a three by eight array of electrodes 122, each of which may be selectively used as either the stimulus electrode or sense electrode, or both.

Figure 2:
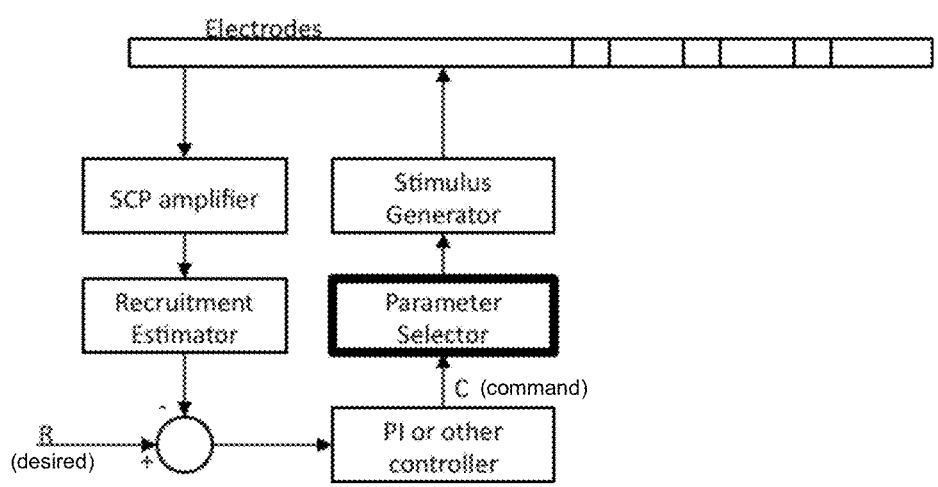
FIG. 2 is a schematic of a feedback controller which refines future stimuli based on estimated recruitment of neurons by past stimuli.

FIG. 2 is a schematic of a feedback controller which refines future stimuli based on estimated recruitment of neurons by past stimuli. The present embodiment provides for the recruitment estimator in FIG. 2 to obtain a measurement of a masked neural response arising in response to a probe stimuli applied during a refractory period of a therapeutic stimulus, and also provides for measurement of an unmasked neural response arising in response to a probe stimuli applied after a refractory period of the same or equivalent subsequent therapeutic stimulus. Comparing the ratio or difference between the masked and unmasked neural responses indicates a level of recruitment achieved by the therapeutic stimulus.

In this embodiment the evoked CAP measurements are made by use of the neural response measurement techniques set out in the Australian provisional patent application No. 2011901817 in the name of National ICT Australia Ltd entitled "Method and apparatus for measurement of neural response" from which the present application claims priority.

Figure 3:
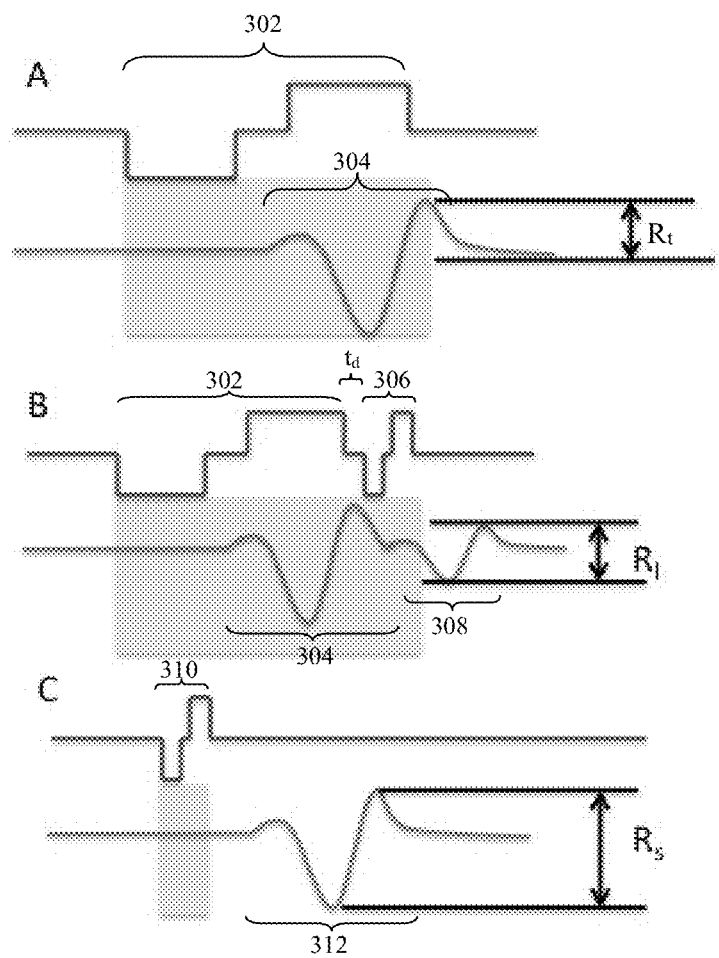
FIG. 3 illustrates the masked to unmasked stimulation paradigm provided by the present embodiment of the invention.

Long pulse widths on the order of 400 μs, as used in many commercially available stimulators, cause problems for the measurement of evoked response, as much of the neural response passes the recording electrodes during the stimulus period. That is, in such a biphasic pulse, at least 0.8 ms passes from stimulus onset before measurement is possible. As shown in FIG. 3A, the therapeutic stimulus 302 continues for a sufficiently long period of time that it substantially temporally overlaps the evoked neural response 304. The signal amplitudes in FIG. 3 are not to scale, and the therapeutic stimulus is of the order of volts while the neural response measurement is of the order of tens of microvolts, so that in the case shown in FIG. 3A the evoked response is practically impossible to measure directly. Nevertheless, for many reasons it is desirable to measure or estimate the amplitude of the response $R_t$ induced by stimulus 302.

FIG. 3B and FIG. 3C illustrate the masked to unmasked stimulation paradigm provided by the present embodiment of the invention. In order to estimate how many fibres are recruited in the neural response 304 arising from the long therapeutic pulse 302, a shorter probe pulse 306 is delivered shortly after the therapeutic stimulus 302. The neural response 308 caused by probe pulse 306 is not contemporaneous with any stimulus, and is therefore able to be measured without being swamped by large stimulus voltages. Notably, by delivering the probe pulse 306 during the refractory period of the fibres triggered in response 304, the response 308 has an amplitude $R_f$ which is proportional to the number of fibres which were not triggered by the long pulse 302.

After a time delay of sufficient length to allow all fibres triggered as part of either response 304 or response 308 to exit their refractory states, another short probe pulse 310 is delivered as shown in FIG. 3C. Probe pulse 310 preferably has the same parameters as probe pulse 306.

Obtaining a measure of response 312 provides an unmasked response amplitude measurement $R_S$, with $R_S > R_f$, against which the first, masked response 308 can be compared. This masked/unmasked ratio ($R_f$:$R_S$) can be used to estimate what proportion of the accessible fibre population was stimulated in response 304 by therapeutic stimulus 302, thereby allowing $R_t$ to be estimated. Notably, when performed sufficiently quickly that a fibre-to-electrode distance will remain substantially constant, this technique is not susceptible to the problem of unknown fibre-to-electrode distance as the ratios cancel the effect of variable electrode-to-fibre distance.

In addition to determining recruitment of long pulse width stimuli, it can be useful to measure physiological parameters such as refractory periods in order to give a diagnosis of various conditions or diseases. Thus, in another embodiment of the invention the refractory period is estimated by first obtaining a measure $R_S$ of the unmasked neural response to a given probe stimulus. Then, two stimuli are applied close together separated by a variable delay $t_d$ (FIG. 3b). With increasing $t_d$, the amplitude $R_f$ can be expected to markedly increase when the onset of pulse 306 is delayed sufficiently to allow the average refractory period of the neural population recruited in response 304 to conclude, so that observing such an increase in $R_f$ allows that population's refractory period to be estimated. There are a number of neurological conditions and non-neurological conditions which can affect the refractory period. This measurement technique may thus serve as a useful diagnostic indicator.

Figure 4:
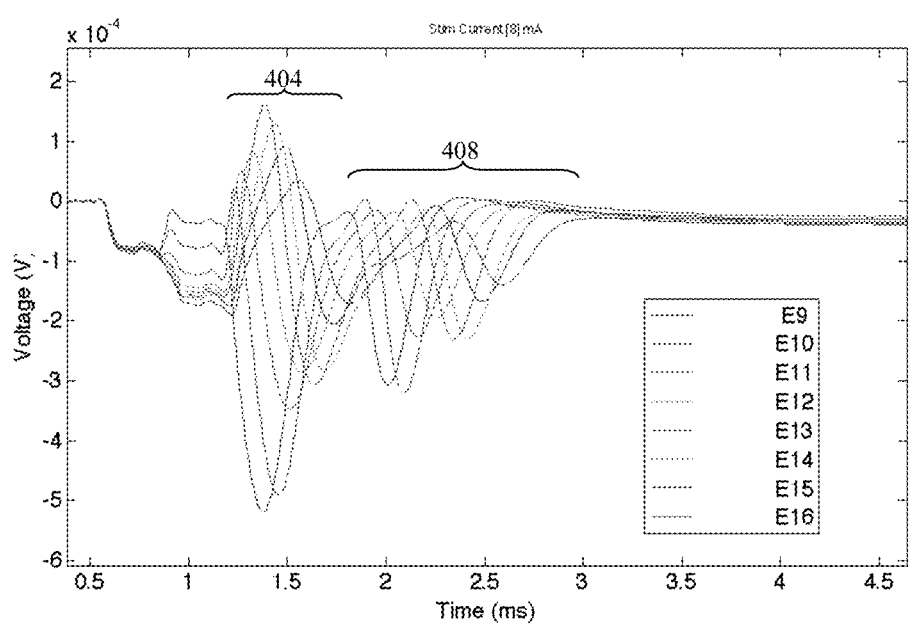
FIG. 4 illustrates recordings of actual evoked responses in accordance with the method of one embodiment of the present invention.

FIG. 4 illustrates recordings of actual evoked responses in accordance with the embodiment of FIG. 3. The recordings of a response pair were made on 8 spaced apart electrodes along the spinal column as the evoked responses 404, 408 travelled along the spinal column adjacent to the array. As can be seen, an initial response 404 is evoked by a first stimulus, and then a second response 408 is evoked immediately afterwards in the refractory period of the neural population recruited as part of response 404. Response 408 is of reduced, but non-zero, amplitude. The relative ratios of the amplitudes of the measurements of the two responses thus permit the above-described information to be elicited.

Figure 5:
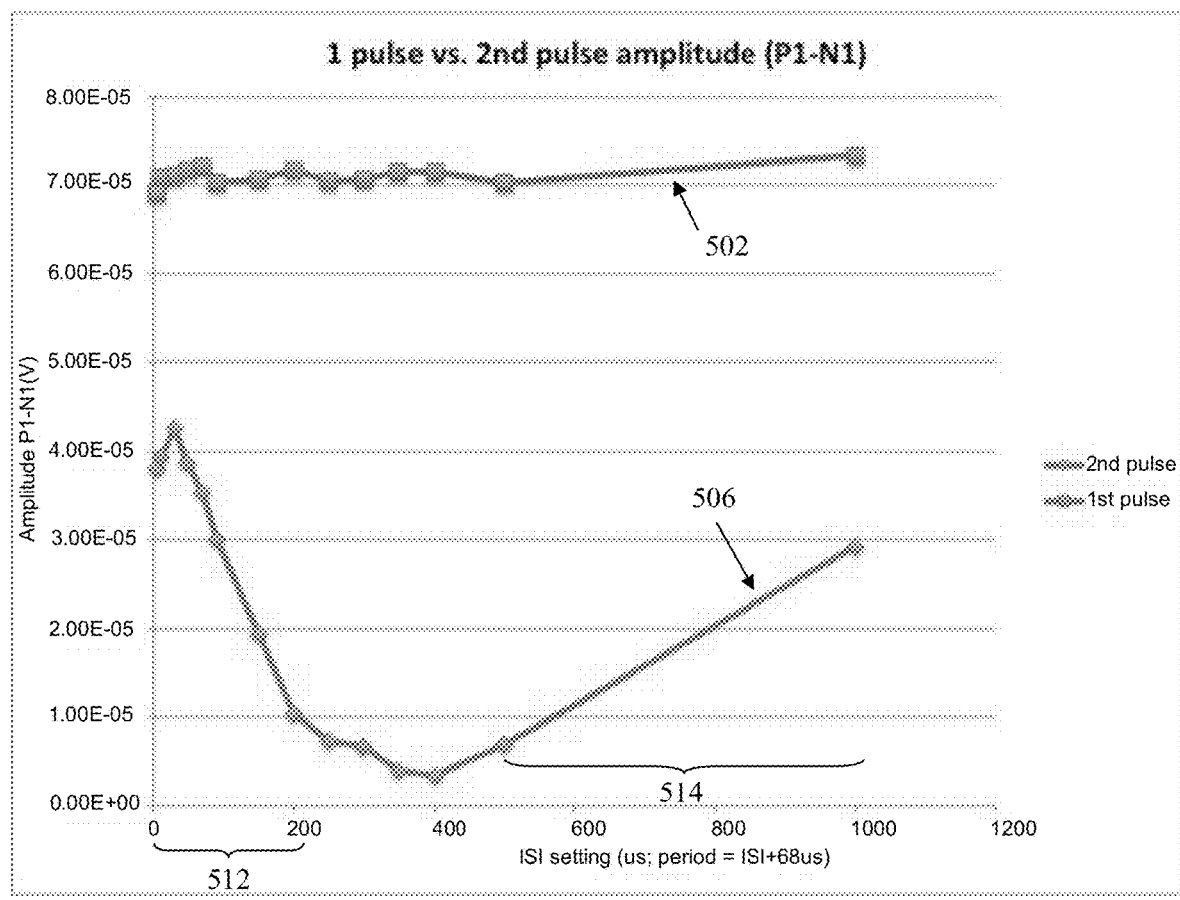
FIG. 5 is a plot of the (P1-N1) amplitude of measurements of responses evoked by two pulses, for varying inter-stimulus interval.

FIG. 5 is a plot of the (P1-N1) amplitude of measurements of responses 502, 506 respectively evoked by a first pulse 302 and a second pulse 306 of equal amplitude and pulse width, for varying inter-stimulus interval $t_d$. As can be seen at 502, the first pulse 302 produces the same recruitment and response amplitudes irrespective of $t_d$. However, the recruitment effected by the second pulse 306 varies considerably with $t_d$, as shown by 506. Two fibre population characteristics are evident in this plot, either or both of which may be investigated in accordance with the present invention in order to determine suitable stimulus parameters and/or physiological state or change. First, pulse 302 will depolarise some fibres close to threshold, but without activating them. This partial depolarisation means that for small $t_d$, in the range (512) of about 0 to 200 μs, where pulse 306 is sufficiently close in time to pulse 302, some fibres that had not been activated by 302 may be activated by 306 more easily than is the case for the remainder of the refractory period for $t_d$>200 μs. This depolarisation will decay with time, usually to resting levels before the end of the absolute refractory period for the fibres that were activated by 302. This means for short inter-stimulus intervals (e.g. <200 us), there will be a response 308 from fibres which had residual depolarisation from 302. Second, for $t_d$ greater than about 400 μs, a relative refractory period 514 commences, during which fibres activated by 302 gradually become able to be activated again. Between the remnant depolarisation period 512 and the relative refractory period 514, the absolute refractory period dominates and the second pulse 306 is almost entirely unable to recruit any response (it is noted that curve 506 is at levels around 5 μV in this period which may be noise and does not necessarily indicate any response has been evoked). Thus assessing curve 506 instantaneously permits a current state of both (a) the residual depolarisation decay 512, and (b) onset of the relative refractory period 514 to be assessed. Monitoring curve 506 over time permits changes in these characteristics to be determined, for example to be used for feedback to optimise therapeutic stimuli or in order to diagnose or monitor an underlying disease.

While FIG. 3B shows the probe pulse 306 as having the same amplitude as therapeutic pulse 302, alternative embodiments may advantageously use probe pulses 306 and/or 310 which are of a different amplitude to therapeutic pulse 302. For example, therapeutic pulse 302 is usually set to a comfortable level for the patient, and at such a level not all fibres are usually recruited by pulse 302. Pulse 306 may therefore be set to have a greater amplitude and/or a greater total charge than therapeutic stimulus 302 in order to ensure that the probe pulse 306 will recruit at least some fibres even when applied during the refractory period of fibres recruited as part of response 304.

In another embodiment the probe stimulus 306 may be configured to have reduced recruitment capability as compared to pulse 302, so that if pulse 306 is applied during the absolute refractory period of fibres recruited as part of response 304 then pulse 306 will recruit no additional response. In such embodiments, when the relative delay $t_d$ is such that probe stimulus 306 occurs in the relative refractory period of response 304, being the period in which some fibres recruited as part of response 304 have concluded their refractory period but some have not, then the probe stimulus response 308 will begin to recruit fibres. Determining the value of $t_d$ at which a threshold exists for response 308 starting to arise provides useful information regarding the refractory period of response 304.

Routinely, during assessment of patients for spinal cord stimulation therapy, the patient will undergo a trial stimulation procedure. This is where the patient is implanted with a percutaneous lead with an externalised set of contacts. The lead is attached to an external pulse generator and the patient has use of the device for several days. At the end of the trial period the clinician and patient assess the performance of the system with regard to pain relief and a choice is made whether or not to proceed with a full implantation. The take-home device for trial purposes may consist of both a stimulus generator but also an evoked response measurement system. The ERT responses recorded during the trial period could be used to adjust the stimulus parameters as described above.

The ERT system measures amplitude growth functions etc., collected at time of surgery and during the trial stimulation period, and together with subjective performance measures could be used to develop a correlation between the response parameters and the patient outcomes. For instance, there is considerable variation in threshold response and there may exist a correlation between threshold and outcome where lower thresholds generate better outcomes. There are a large number of neurological parameters that can be collected in performing ERT measures, including refractory periods. Systematic collection of this data across a number of patients will allow analysis for correlation with outcome.

It will be appreciated by persons skilled in the art that numerous variations and/or modifications may be made to the invention as shown in the specific embodiments without departing from the spirit or scope of the invention as broadly described. For example the neural response measurement may be conducted in accordance with any suitable CAP measurement technique. The present embodiments are, therefore, to be considered in all respects as illustrative and not restrictive.

Figure 6:
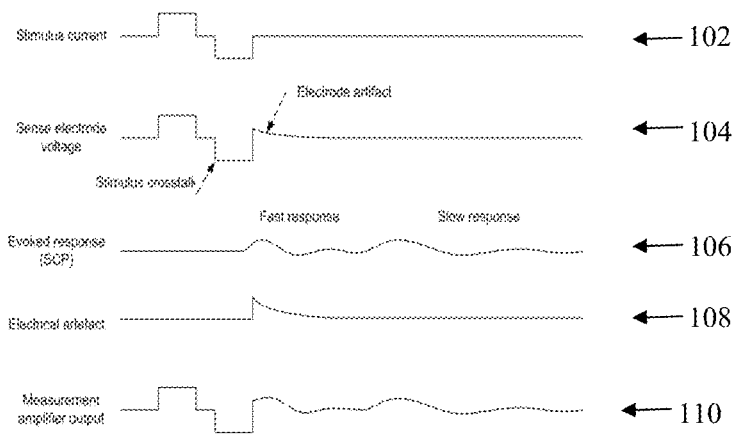
FIG. 6 illustrates currents and voltages which can contribute to SCP measurements.

FIG. 6 shows the currents and voltages that contribute to SCP measurements. These signals include the stimulus current 102 applied by stimulus electrodes, which is a charge-balanced biphasic pulse to provide low artefact. In the case of spinal cord stimulation, the stimulus currents 102 used to provide paraesthesia and pain relief typically consist of pulses in the range of 3-30 mA amplitude, with pulse width typically in the range of 100-400 µs. The stimuli can comprise monophasic or biphasic pulses.

The stimulus 102 induces a voltage on adjacent electrodes, referred to as stimulus crosstalk 104. Where the stimuli 102 are SCP stimuli they typically induce a voltage 104 in the range of about 1-5 V on a SCP sense electrode.

The stimulus 102 also induces electrode artefact, which is a residual voltage on an electrode resulting from uneven charge distribution on its surface. The electrode artefact is indicated in the voltage waveform 104 after cessation of stimulus crosstalk. The stimulus 102 disturbs the galvanic interface between the sense electrode and the tissue, so that after stimulus crosstalk in voltage 104 concludes, a voltage known as the electrode artefact continues on the electrode, as indicated in waveform 104 in FIG. 6. Electrode artefact is very difficult to measure, and depends on factors such as the stimulation pulse, the geometry of the electrodes and the bio-electrical nature of the tissue surrounding the electrodes. Electrode artefact can have a typical value of 50 µV at a time 50 µs after stimulation ceases. Electrode artefact is difficult to measure because it is indistinguishable from electrical artefact, the latter being caused by the amplifier's exposure to the high stimulation voltages. Further, the causes of electrical artefact can be subtle, and therefore hard to identify and eliminate.

An appropriate stimulus 102 will also induce nerves to fire, and thereby produces an evoked neural response 106. In the spinal cord, the neural response 106 has two major components: a fast response lasting ~2 ms and a slow response lasting ~15 ms. The amplitude of the evoked response seen by epidural electrodes is typically no more than hundreds of microvolts, but in some clinical situations can be only tens of microvolts.

In practical implementation a measurement amplifier used to measure the evoked response does not have infinite bandwidth, and will normally have infinite impulse response filter poles, and so the stimulus crosstalk 104 will produce an output 108 during the evoked response 106, this output being referred to as electrical artefact. Electrical artefact can be in the hundreds of millivolts as compared to a SCP of interest in the tens of microvolts. Electrical artefact can however be reduced by suitable choice of a high-pass filter pole frequency.

The measurement amplifier output 110 will therefore contain the sum of these various contributions 102-108. Separating the evoked response of interest (106) from the artefacts 104 and 108 is a major technical challenge. For example, to resolve a 10 µV SCP with 1 µV resolution, and have at the input a 5V stimulus, requires an amplifier with a dynamic range of 134 dB. As the response can overlap the stimulus this represents a difficult challenge of amplifier design.

Figure 7A:
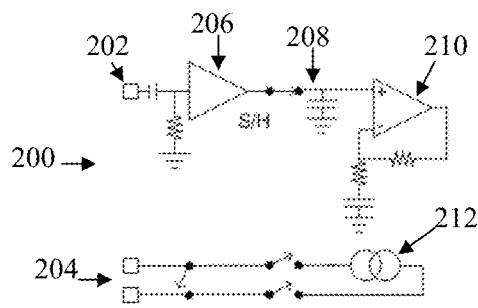
FIG. 7A, FIG. 7B, FIG. 7C, FIG. 7D and FIG. 7E illustrate the circuitry of one embodiment of the present invention, throughout five phases of a measurement cycle.

FIG. 7A is a schematic diagram of the first of five phases of operation of a sample and hold (S/H) measurement amplifier in accordance with one embodiment of the present invention. The stimulus and measurement circuitry 200 comprises a buffer amplifier 206 that is always connected to the sense electrode 202 such that there is no switch between the sense electrode 202 and the buffer amplifier 206. The output of the buffer amplifier 206 drives a sample and hold circuit 208, followed by a high gain amplifier 210 with unity gain at DC. The front-end amplifier 206 has sufficiently wide bandwidth that it can follow the voltage induced on the sense electrodes 202 by the stimulus pulse, and settle before the SCP begins. A current source 212 can be selectively connected to stimulus electrodes 204 to deliver a stimulus. The stimulus electrodes 204 and sense electrode 202 are in the same electrode array of a single implanted device.

The stimulus and measurement circuitry 200 operates to obtain a SC measurement using five phases. The first phase shown in FIG. 7A open circuits the stimulus electrodes 204 and connects the sense electrode 202 to the measurement amplifier 210 by setting the sample and hold circuit to "sample". The first phase shown in FIG. 7A allows the amplifier chain 206, 210 to settle, with no disturbance from the stimulating electrodes 204.

Figure 7B:
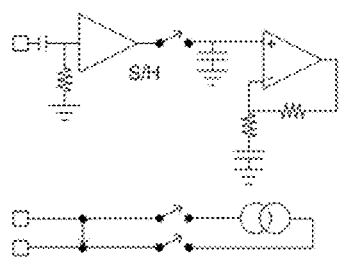

FIG. 7B is a schematic diagram of the second of five phases of operation of a sample and hold (S/H) measurement amplifier in accordance with one embodiment of the present invention. The stimulus and measurement circuitry 200 comprises a buffer amplifier 206 that is always connected to the sense electrode 202 such that there is no switch between the sense electrode 202 and the buffer amplifier 206. The output of the buffer amplifier 206 drives a sample and hold circuit 208, followed by a high gain amplifier 210 with unity gain at DC. The front-end amplifier 206 has sufficiently wide bandwidth that it can follow the voltage induced on the sense electrodes 202 by the stimulus pulse, and settle before the SCP begins. A current source 212 can be selectively connected to stimulus electrodes 204 to deliver a stimulus. The stimulus electrodes 204 and sense electrode 202 are in the same electrode array of a single implanted device.

In the second phase shown in FIG. 7B, the stimulus electrodes 204 are short circuited to each other. This allows the stimulating electrodes 204 to recover charge, so as to avoid DC injection to the tissue as is required for electrical implants. During this phase, the sample-and-hold 208 is set to "hold" so that charge transfer on the stimulus electrodes 204 does not disrupt the measurement amplifier 210.

Figure 7C:
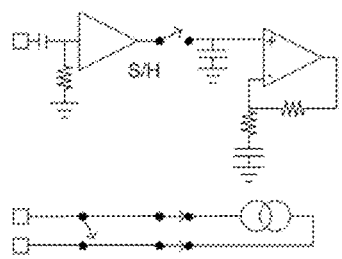

FIG. 7C is a schematic diagram of the third of five phases of operation of a sample and hold (S/H) measurement amplifier in accordance with one embodiment of the present invention. The stimulus and measurement circuitry 200 comprises a buffer amplifier 206 that is always connected to the sense electrode 202 such that there is no switch between the sense electrode 202 and the buffer amplifier 206. The output of the buffer amplifier 206 drives a sample and hold circuit 208, followed by a high gain amplifier 210 with unity gain at DC. The front-end amplifier 206 has sufficiently wide bandwidth that it can follow the voltage induced on the sense electrodes 202 by the stimulus pulse, and settle before the SCP begins. A current source 212 can be selectively connected to stimulus electrodes 204 to deliver a stimulus. The stimulus electrodes 204 and sense electrode 202 are in the same electrode array of a single implanted device.

In the third phase shown in FIG. 7C, the stimulation is applied. The stimulus electrodes 204 are switched to the current source 212, and the sample-and-hold 208 is set to "hold" so that the large stimulus crosstalk seen on electrode 202 is not presented to the measurement amplifier 210.

Figure 7D:
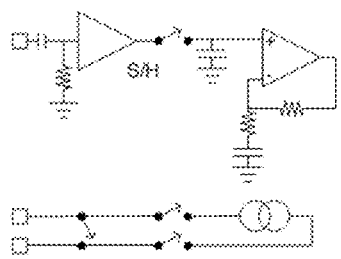

FIG. 7D is a schematic diagram of the fourth of five phases of operation of a sample and hold (S/H) measurement amplifier in accordance with one embodiment of the present invention. The stimulus and measurement circuitry 200 comprises a buffer amplifier 206 that is always connected to the sense electrode 202 such that there is no switch between the sense electrode 202 and the buffer amplifier 206. The output of the buffer amplifier 206 drives a sample and hold circuit 208, followed by a high gain amplifier 210 with unity gain at DC. The front-end amplifier 206 has sufficiently wide bandwidth that it can follow the voltage induced on the sense electrodes 202 by the stimulus pulse, and settle before the SCP begins. A current source 212 can be selectively connected to stimulus electrodes 204 to deliver a stimulus. The stimulus electrodes 204 and sense electrode 202 are in the same electrode array of a single implanted device.

The fourth phase shown in FIG. 7D provides for a post-stimulus delay. In this phase the stimulus electrodes 204 are open circuited, and the sample-and-hold remains in the "hold" position, to allow the electrodes 202, 204 settle towards equilibrium, as defined by bio-electrical conditions.

Figure 7E:
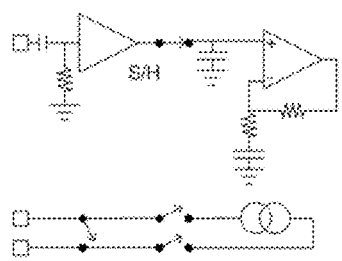

FIG. 7E is a schematic diagram of the fifth of five phases of operation of a sample and hold (S/H) measurement amplifier in accordance with one embodiment of the present invention. The stimulus and measurement circuitry 200 comprises a buffer amplifier 206 that is always connected to the sense electrode 202 such that there is no switch between the sense electrode 202 and the buffer amplifier 206. The output of the buffer amplifier 206 drives a sample and hold circuit 208, followed by a high gain amplifier 210 with unity gain at DC. The front-end amplifier 206 has sufficiently wide bandwidth that it can follow the voltage induced on the sense electrodes 202 by the stimulus pulse, and settle before the SCP begins. A current source 212 can be selectively connected to stimulus electrodes 204 to deliver a stimulus. The stimulus electrodes 204 and sense electrode 202 are in the same electrode array of a single implanted device.

Finally, in the fifth phase shown in FIG. 7E, the SCP present at sense electrode 202 is measured by switching the sample-hold 208 to "sample".

When performing repeated measurement cycles in this fashion, it is noted that the switch positions are the same in the phase 1 "settling" and the phase 5 "measuring" states. Thus, the state of phase 5 is maintained, by virtue of a subsequent phase 1, until the electrodes and circuitry are in equilibrium, even after the time that useful SCP data is no longer present or being captured. Such embodiments thus provide a greater length of the "settle" state.

Figure 8:
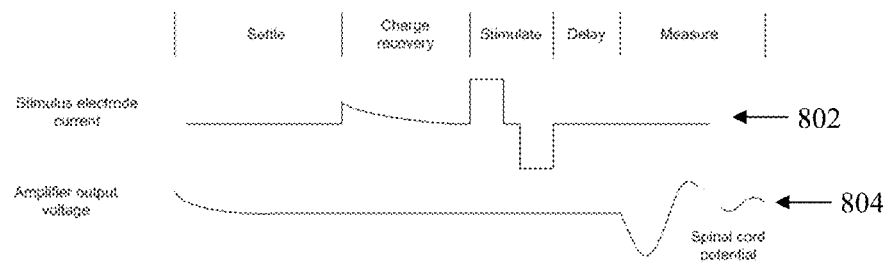
FIG. 8 illustrates idealised waveforms arising in the circuit of FIG. 2 during each phase of the measurement cycle.

FIG. 8 shows idealised waveforms arising during the SCP measurement process of FIG. 7A, FIG. 7B, FIG. 7C, FIG. 7D, and FIG. 7E. FIG. 8 illustrates the current 802 of stimulus electrodes 204, and the output voltage 804 of amplifier 210, during each of the five phases of the measurement cycle. Importantly, it can be seen that phase 1 permits the amplifier bias point to settle to a steady state as defined by bio-electrical conditions at the sense electrode, while phases 2-4 do not disrupt the amplifier 210 bias point.

An advantage of this circuit is that in the phase 2 equilibration, the circuitry around amplifier 210 is a low-pass filter, and is therefore relatively immune to noise and input transients. This also allows the amplifier 210 to accumulate its bias point over successive measurement cycles, as it does not need to be reset for each cycle. Moreover, because of the buffer 206 before the sample/hold 208, the input-referred effect (i.e. the effect upon sense electrode 202) of the charge injection into the sample/hold 208 is lower.

In the embodiment of FIG. 7A, FIG. 7B, FIG. 7C, FIG. 7D, and FIG. 7E, the sense electrode 202 is never shorted to the stimulus electrodes 204, recognising that this creates dis-equilibrium in the sense electrodes and adds artefact, rather than having the effect of creating equilibrium as previously thought. In some embodiments, it may be possible to overlap the "settle" (equilibrate) phase of FIG. 7A, and the "charge recovery" phase of FIG. 7B, although it would be expected that the artefact would be higher, and the time taken to reach equilibrium longer.

Figure 9:
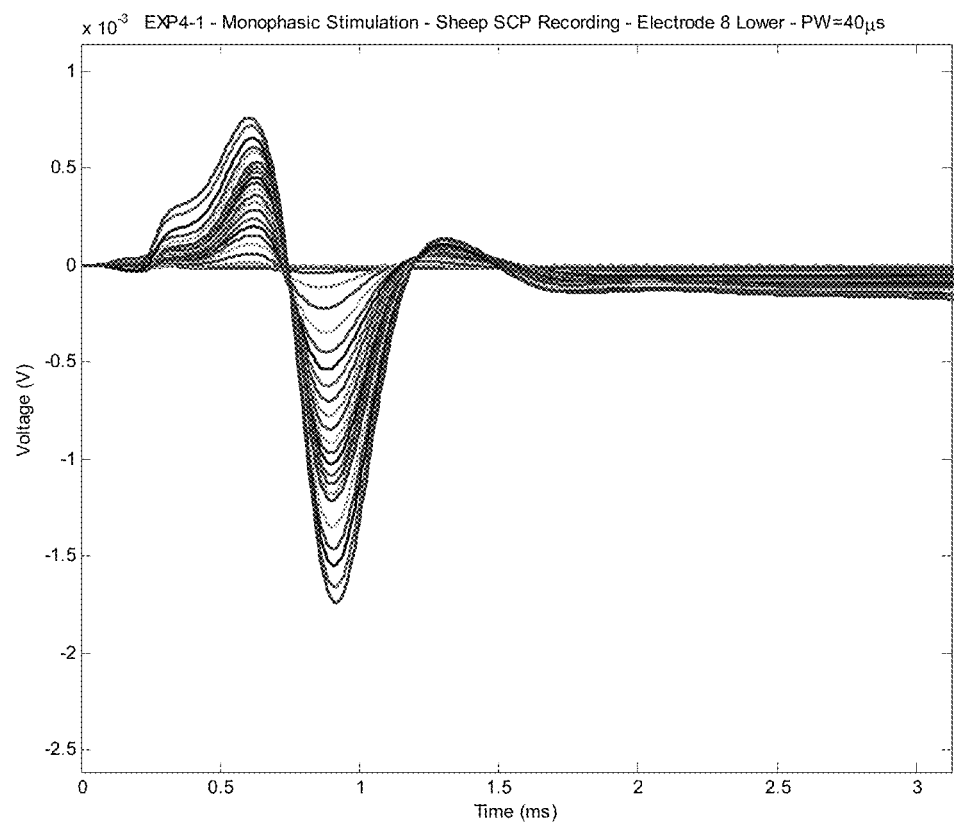
FIG. 9 illustrates SCP measurements made using the embodiment of FIG. 2.

FIG. 9 is a plot of 22 separate measurements of ovine SCP made using the embodiment of FIG. 7A, FIG. 7B, FIG. 7C, FIG. 7D, and FIG. 7E. The measurements were obtained sequentially for differing stimuli, the stimuli comprising biphasic current pulses of 40 μs pulse width and a current amplitude which varied from 0-10 mA. The measurements were then plotted on a single chart to produce FIG. 9.

The waveforms of FIG. 9 have lower dynamic range and simpler morphology than measurements produced by previous approaches, due to the absence of stimulus crosstalk and reduced artefact. When wishing to provide a system built on an implanted integrated circuit, wide dynamic range amplifiers are difficult to design, as are signal processing systems for feature extraction. Beneficially, the nature of the measured waveforms shown in FIG. 9 permits, for example, a circuit for extracting the peak-to-peak SCP amplitude to have fewer components than would be required to operate upon the waveform produced by previous approaches. Thus the techniques of the present invention for artefact reduction greatly assist in building a practical implanted, evoked response feedback system.

Moreover, it is notable that in this case of a 40 μs pulse width the measurement system is settled and ready to record prior to onset of the evoked CAP. The sense electrode was less than 50 mm from the stimulus electrode, and a post-stimulus delay of 50 μs was observed before the measurement amplifier was switched in to obtain the recordings shown in FIG. 9.

Figure 10:
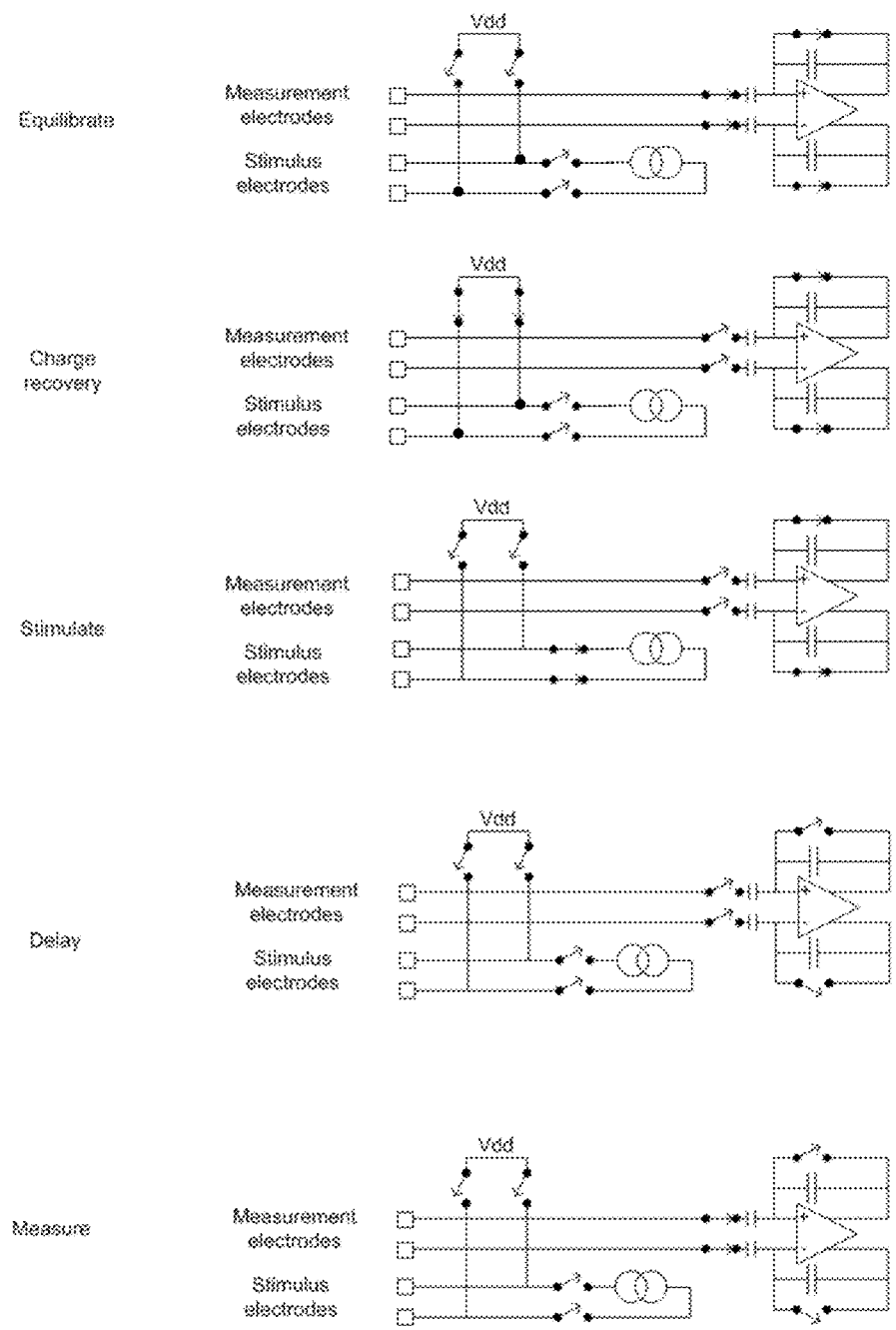
FIG. 10 illustrates the circuitry of an alternative embodiment of the invention implementing differential CAP measurements.

FIG. 10 illustrates the circuitry of an alternative embodiment of the invention in which a differential measurement amplifier is used, and charge recovery is via a voltage rail $V_{dd}$. As can be seen, in accordance with the present invention the measurement phases are carried out in a corresponding manner despite the use of different hardware.

Figure 11:
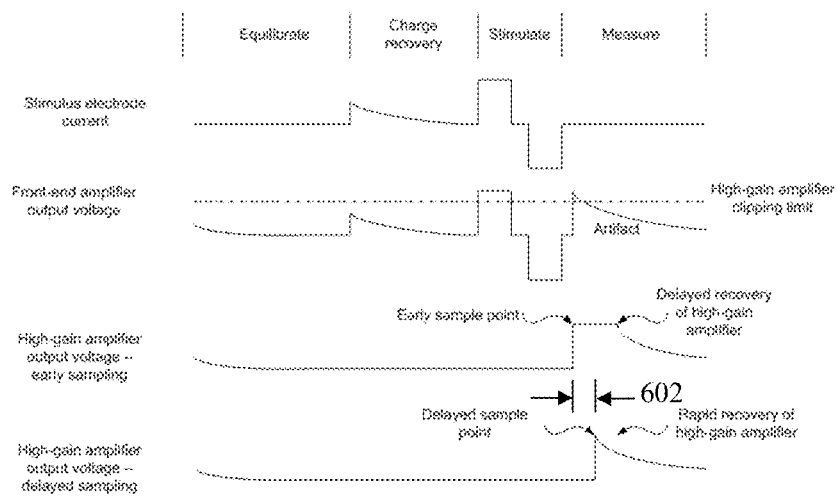
FIG. 11 illustrates delayed activation of a measurement amplifier to avoid clipping.

In the embodiments of either FIG. 7A, FIG. 7B, FIG. 7C, FIG. 7D, and FIG. 7E or FIG. 10, artefact can cause the high-gain measurement amplifier 210 to clip, and the amplifier can subsequently be slow to recover. However, in preferred embodiments the sample point, being the transition from the "stimulate" to "measure" phases, is delayed, allowing clipping to be avoided. FIG. 11 illustrates the manner of determining a suitable delay 602. Such embodiments may permit use of a higher amplifier gain than would otherwise be the case. In particular, a variable delay and increased amplifier gain may be particularly apt in circumstances where high-gain is desired, and parts of the SCP of interest do not immediately follow the stimulation. Thus, delaying the start of measurement will avoid the side effects of clipping.

Figure 12:
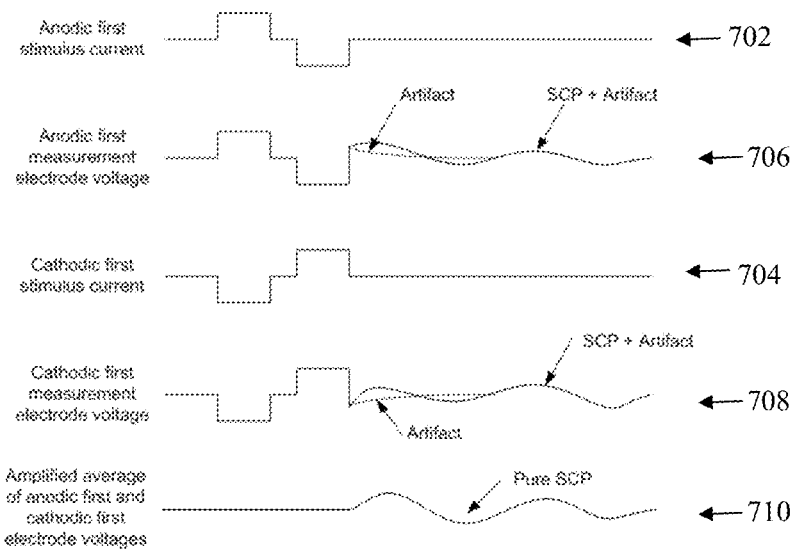
FIG. 12 illustrates an embodiment in which alternate phased stimuli are used to obtain an averaged CAP measurement.

In another embodiment of the invention shown in FIG. 12, a method to eliminate artefact from an SCP measurement is to alternate the phase of stimulus waveforms and take an average of obtained measurements. FIG. 12 shows the stimulus current for a positive "anodic-first" stimulus 702, and the stimulus current for a negative "cathodic first" stimulus 704. In this embodiment these are applied in succession with respective CAP measurements obtained after each stimulus. The respective measurement electrode voltages 706 and 708 arising from each such stimulus are also shown. It will be observed where indicated in waveforms 706, 708 that the artefact from each of the two stimuli are of identical magnitude, but opposite sign. In most situations it will be found that the artefact polarity depends on the stimulus polarity. An example of this would be electrical artefact caused by the high-pass poles of the front-end amplifier 206. Clearly, either phase could be used for stimulating nervous tissue, though their effects will differ.

In contrast, the positive and negative phase stimuli 702, 704 produce SCPs of differing amplitudes, but approximately similar shape and importantly of similar polarity, as this is determined by the anatomy and physiology of the spinal cord membrane. Thus, when the voltages 706, 708 resulting from the positive and negative phase stimuli 702, 704 are recorded, and averaged, the opposite phase stimulation artefacts substantially cancel, leaving the SCP or a combination of the two SCPs 710. Note that in practical situations, the artefact can have much higher amplitude than the SCP, making it much harder to detect the SCP than is apparent from FIG. 12.

The response of the spinal cord to these two polarities of stimulation are referred to as the "anodic first" and "cathodic first" SCP responses, as referred to the electrode considered to be that closest to the recording electrode. I.e. anodic-first stimulation makes the stimulating electrode closest to the sense electrode anodic in the first phase of stimulus. Usually cathodic-first stimulation has a lower threshold for neural activation than is the case for anodic-first stimulation. Nevertheless, the SCP polarity is independent of whether the stimulus is anodic first 702 or cathodic first 704.

Figure 13A:
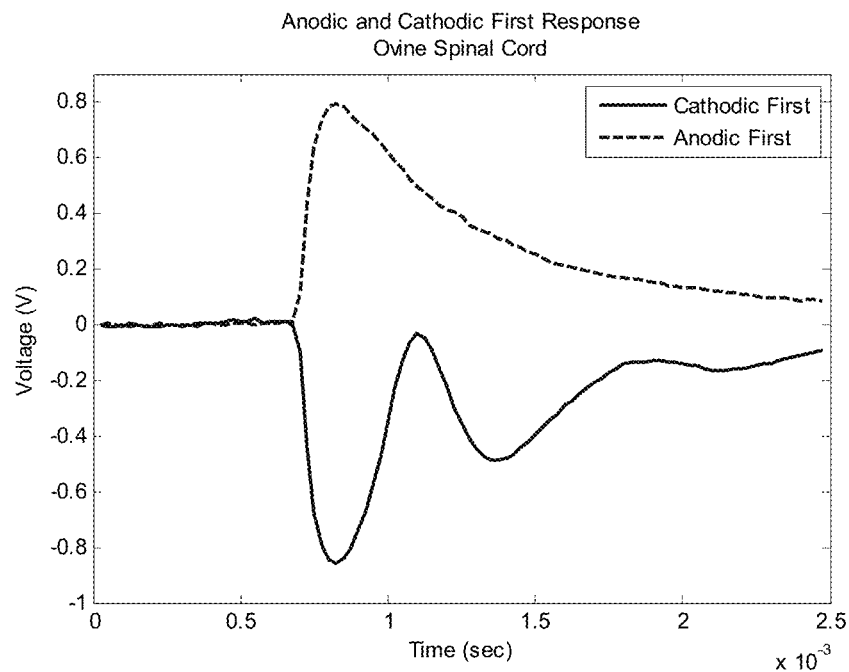

FIG. 13A illustrates spinal cord measurements obtained in response to anodic-first and cathodic-first stimulations, respectively. Note that measurement obtained in response to the anodic-first stimulation lacks the characteristic P1-N1-P2 form, indicating that the anodic-first stimulation did not evoke a neural response in this case. In contrast, the measurement obtained in response to the cathodic-first stimulus exhibits a significant evoked neural response.

Figure 13B:
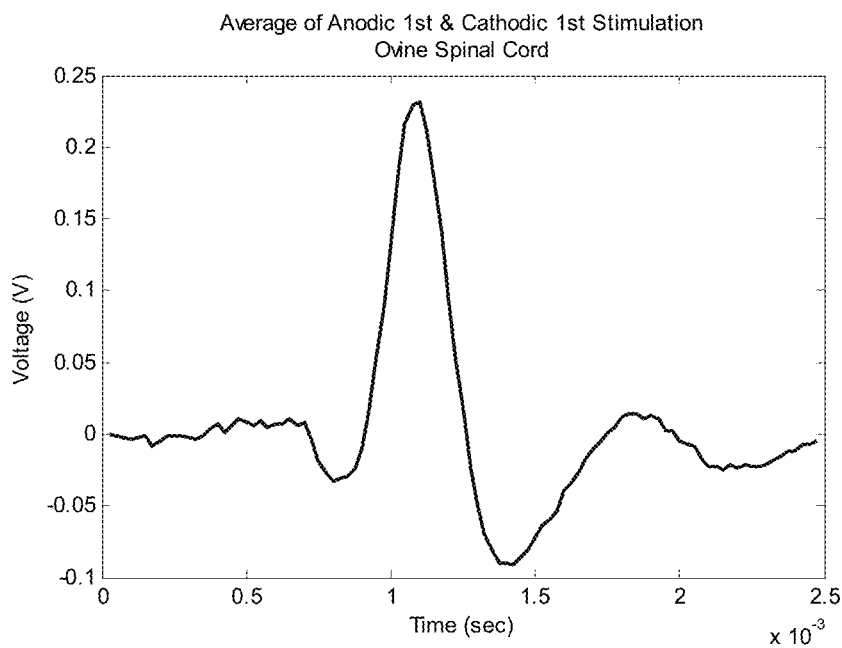
FIG. 13B illustrates the averaged measurement obtained therefrom.

FIG. 13B shows an average of the two responses in FIG. 15A. As can be seen, while the characteristic form of the SCP has been altered, the artefact is essentially removed.

Figure 14:
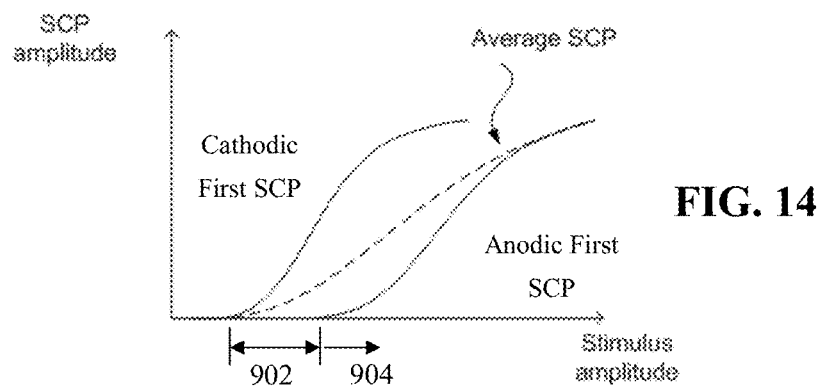
FIG. 14 illustrates the CAP response to anodic-first and cathodic-first stimuli, respectively, with increasing stimulus amplitude.

This embodiment of the invention further recognises that the averaged waveform of FIG. 13B can be used to obtain a range of information despite the atypical SCP form. In this regard, FIG. 14 illustrates SCP growth curves against stimulus amplitude, for both anodic-first and cathodic-first stimuli. FIG. 14 also shows the growth behaviour of the average SCP against stimulus amplitude. It can be seen from FIG. 14 that the threshold of the average response is identical to the threshold of the more sensitive cathodic-first stimulation.

When the stimulus amplitude is in the range 902 such that only the cathodic-first stimulus produces an SCP, then the averaged SCP waveform would have a normal SCP morphology but would be half the amplitude compared to a true cathodic first SCP due to the averaging. In the region 904 where both the anodic first and cathodic first responses contribute to the averaged SCP, the resultant averaged SCP waveform will have morphology in between the two measurements. It would not directly represent an SCP, but rather the average of two different SCPs. Nevertheless, this waveform could still be valuable for example in implementing an automatic control loop for stimulation adjustment, as it gives a value proportional to neural recruitment.

Some embodiments of the invention, such as the embodiment of FIG. 10, may use differential amplifiers so as to detect the voltage difference between two sense electrodes. Differential amplifiers simplify the task of separating electrode artefact. If they are connected to electrodes with similar area, and separated from the stimulation electrodes in a similar manner, then they receive similar levels of electrode artefact and this will be removed when their difference voltage is obtained. However, in such a system the voltage recorded by the amplifier is the difference between the voltages at two points along a bundle of neurons, and can thus be difficult to interpret. When making SCP measurements, it is preferable to use single-ended amplifiers as they more accurately measure the SCP, and they are more sensitive in measuring the SCP.

Figure 15:
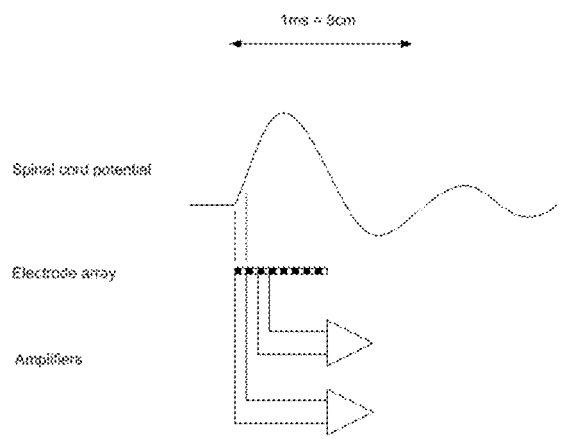
FIG. 15 illustrates the nature of differential CAP measurements in the spinal cord.

Differential amplifiers are often used because they provide a means to reduce electrode artefact, when other means have been insufficient. However, FIG. 15 illustrates a problem of measuring SCPs with differential amplifiers. It shows a spinal cord potential. As this potential travels along the spine at a velocity, which can be as high as 80 m·s-1, it can also be considered as a spatial wave. Given that a peak-to-peak cycle of the fast response of an SCP typically lasts for 1 ms, the wave will travel 8 cm in this time. Using this 1 ms=8 cm scale, a 5 cm electrode array is drawn alongside the SCP in FIG. 15. Connected to this electrode array are two amplifiers configured to make differential SCP measurements from separate pairs of sense electrodes. As can be seen from FIG. 15, the difference between the voltages on the adjacent electrodes will be quite small and significantly smaller than the peak to peak amplitude of the SCP, and thus more susceptible to electrical noise generated by the amplifier. The output of the amplifier will approximate the differential of the SCP, and thus be harder to interpret than a simple measure of the SCP itself. If measuring evoked SCPs with a micropackage stimulator design, for example in a system using a two-wire bus, differential measurements between non-adjacent electrodes are not possible. Further, if wishing to measure the slow response of the SCP, which has a period of about 6 ms and correspondingly reduced signal gradients, differential measurements are even more difficult to effect. Thus it will be appreciated that single-ended measurements are preferable, as long as artefact can be kept at a sufficiently low level.

With the measurement sequence of the present invention, the artefact is reduced so that some embodiments may instead use a single-ended amplifier, even in situations where previously they would have suffered from too much electrode artefact. Moreover, trials to date show that recording can be initiated with an extremely short time interval from cessation of the stimulus, permitting the same electrode array to be used for recording and stimulation, and even permitting recordings to be made on the electrode immediately adjacent to the stimulus electrode in an electrode array with electrode spacings of less than 10 mm.

Single ended amplifiers have the further advantage that they consist of fewer capacitors and amplifier components than differential amplifiers, so will take up less space on a silicon chip, which is a significant benefit when intended for use in an implanted system with many electrodes and where the silicon area for each amplifier is limited.

Preferred embodiments of the invention may comprise a separate amplifier chain (e.g. 206, 208, 210, see FIG. 7A, FIG. 7B, FIG. 7C, FIG. 7D, and FIG. 7E) for every electrode, organised in parallel manner, permitting simultaneous recording of a single CAP from multiple sense electrodes in parallel, and also eliminating the switching noise arising in systems which switch the sense electrode to a shared measurement amplifier.

Figure 16:
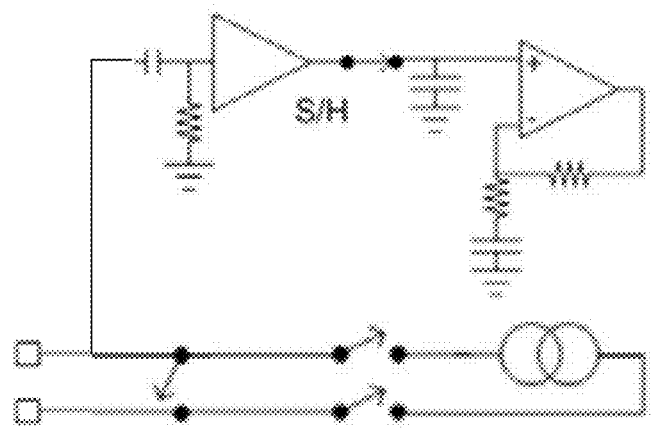
FIG. 16 illustrates yet another embodiment of the invention, in which a single electrode serves both as a stimulus electrode and also as the sense electrode in the same measurement cycle.

FIG. 16 illustrates another embodiment of the invention in which the sense electrode is one of the stimulus electrodes. The follower/buffer amplifier in this embodiment has sufficient dynamic range to withstand the stimulus phase, however in alternative embodiments a switch may be interposed between the measurement electrode and the measurement circuitry to isolate the follower/buffer amplifier during the stimulus phase.

Figure 17A:
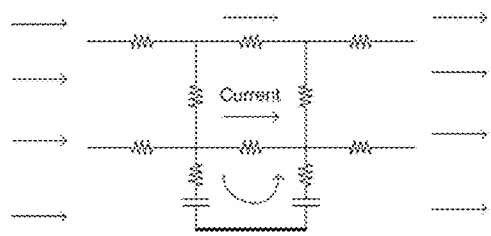
FIG. 17A and FIG. 17B illustrate a model of a metal electrode in a conductive solution.

Further embodiments of the invention may employ divisible electrodes, as discussed below with reference to FIG. 17 and FIG. 18. When considering electrode artefact in particular, the sources of electrode artefact are relatively poorly understood. The surface of a metal electrode can be modelled as an RC network. For an accurate model, an infinite-phase element is required, but for the explanation of artefact a simple RC model will suffice, as shown in FIG. 17A. A conductive solution can be modelled as a mesh of resistors. Where a conductive solution meets a piece of metal of finite dimensions, the metal provides an alternative conduction path to the solution. This charges the electrode-to-tissue capacitances at the "ends" of the electrodes, with opposite polarities. The electrode does not acquire net charge, but it does cease to be in equilibrium. After the external current ceases, then the electrode will pass current through the solution as it re-equilibrates for a short time after the stimulus. This current will affect the potential of another electrode in the solution, and in the case of multielectrode arrays a unique such current will arise at every electrode in response to local conditions experienced at that electrode. The cumulative impact of such reequilibration currents is seen by a sense electrode as electrode artefact.

Figure 17B:
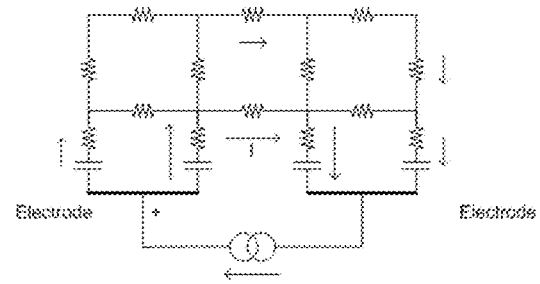

A similar effect happens when current flows between two electrodes, as shown in FIG. 17B. During application of a stimulus, the current preferentially flows between the parts of the electrodes where they are closest. When the current is interrupted, the charge on the surface of the electrodes must re-equilibrate; this also leads to a residual current and contributes to electrode artefact seen by a sense electrode.

Figure 18A:
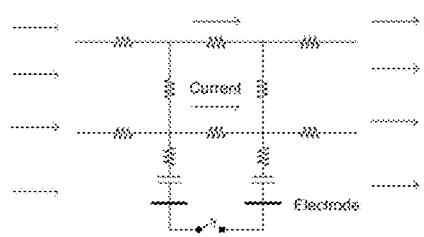
FIG. 18A and FIG. 18B illustrate segmented electrodes which may be used to reduce artefact without sacrificing noise, impedance or current carrying capacity.
Figure 18B:
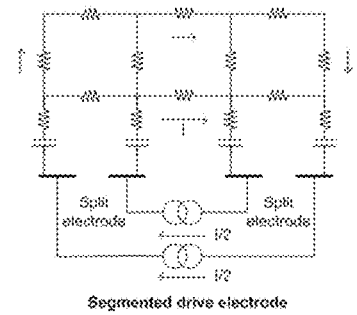

The model of FIG. 17B predicts that using smaller electrodes will reduce artefact. However, smaller electrodes will have higher noise when used as measurement electrodes, and higher resistance and lower current carrying capacity when used as stimulus electrodes. Two means to reduce artefact without sacrificing noise, impedance or current carrying capacity are shown in FIG. 18A and FIG. 18B. The electrode configuration of FIG. 18A reduces artefact induced in a single metallic electrode; the electrode is composed of two or more smaller electrodes that can be disconnected during a stimulation phase, and reconnected during a measurement phase. In the configuration of FIG. 18B, an electrode is segmented, and individual current sources are provided for each segment. This forces the current in the segments to match, and so reduces artefact.

The evoked response telemetry of the present invention may in some embodiments be used to monitor the effect of a delivered compound. The administration of compounds (drugs or other chemical therapeutics) to effect a change in the nervous system is common for treatment of a wide number of diseases and disorders. Anaesthetics of various types are administered to the spinal cord for the relief of pain. Perhaps the most common form is administration of anaesthetics in the epidural space for pain relief during child birth.

In such embodiments, a catheter comprising a drug delivery tube may be fitted with electrode elements and configured to obtain neural response measurements in accordance with the present invention in order to monitor drug-induced effects on the neural response. Alternatively an electrode array may be temporarily or permanently implanted and used to apply neural stimuli and monitor the neural response. The neural response measurements may be obtained repeatedly during administration of the drug in order to directly measure the effect of the administered drug and control the dosage delivered.

Figure 19A:
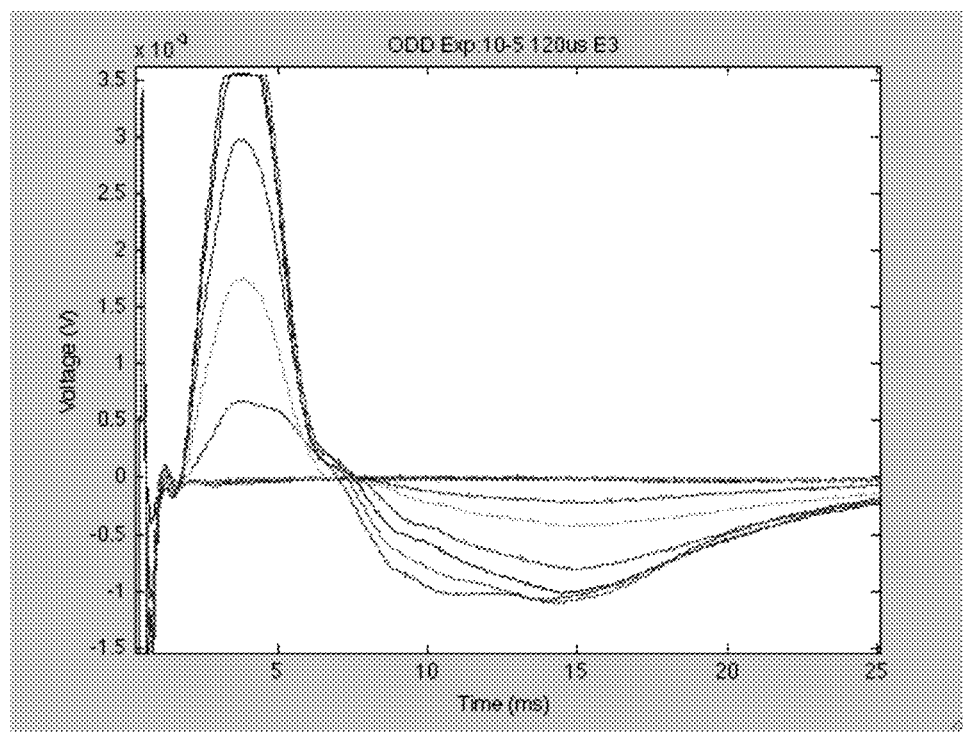
FIG. 19A and FIG. 19B illustrate the effect of epidural administration of Lignocaine on suppression of the spinal evoked responses.
Figure 19B:
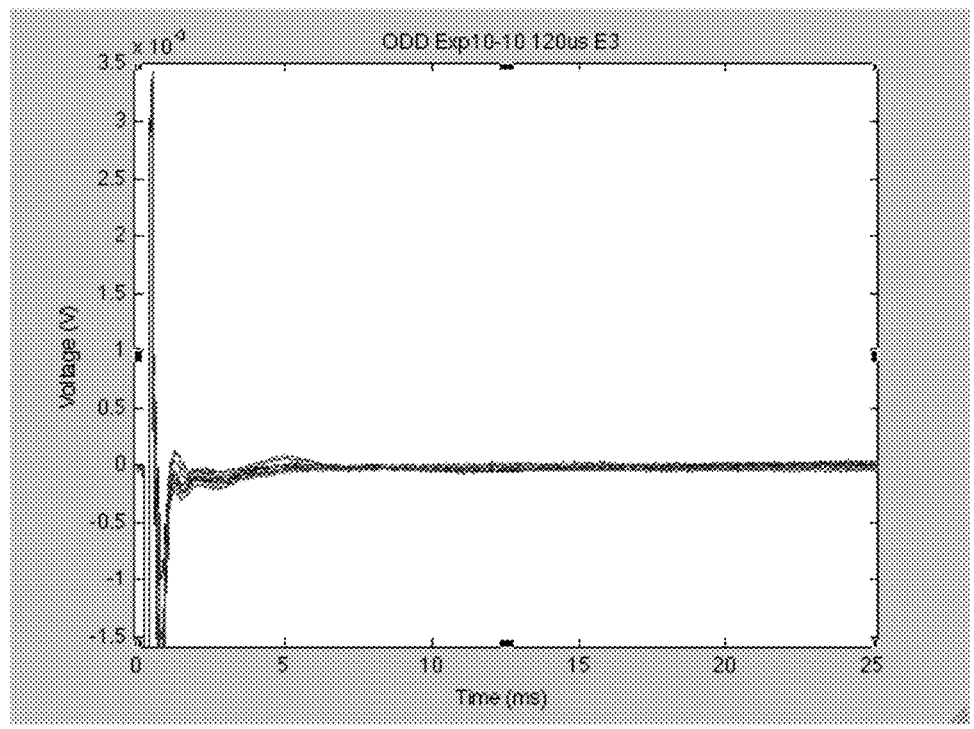

FIG. 19A and FIG. 19B illustrate the effect of administration of anaesthetic to the spinal cord, with a neural response being present prior to administration and largely being absent subsequent to administration. As can be seen, there is a direct correlation between the measured evoked response and the dosage of the anaesthetic. A "partial block" may be effected by ceasing administration of the anaesthetic once the neural response amplitude reduces to a desired level. The technology described herein is suitable for full implantation within the body of a subject and as a result the evoked potential monitoring could be used in the administration of an active compound to produce a therapeutic benefit. The system could be integrated with in an implantable pump to control the administration of the compound.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of applying stimulus to a tissue, the method comprising:
   delivering a therapeutic pulse having a first pulse width via one or more stimulus electrodes, wherein the therapeutic pulse evokes a neural response,
   delivering at least one probe pulse having a second pulse width after the therapeutic pulse, wherein the second pulse width is less than the first pulse width, and
   measuring a neural response subsequent to the therapeutic pulse via one or more sense electrodes:
   determining a neural recruitment caused by the therapeutic pulse based on the neural response; and
   determining a parameter for a subsequent therapeutic pulse based on the neural recruitment.

2. The method of claim 1, wherein the first pulse width is in a range of 100-500 μs.

3. The method of claim 1, wherein the determining the parameter comprises:
   comparing the neural recruitment with a target neural recruitment;
   deriving, using a controller, a command from the comparison; and
   selecting, based on the command, the parameter for the subsequent therapeutic pulse.

4. The method of claim 3, wherein the selecting the parameter comprises refining a parameter for the delivered therapeutic pulse.

5. The method of claim 3, wherein the target neural recruitment is a predetermined neural recruitment.

6. The method of claim 1, further comprising:
   determining a parameter for a subsequent probe pulse based on the neural recruitment.

7. The method of claim 1, wherein the probe pulse is delivered after a refractory period of fibres recruited by the therapeutic pulse.

8. The method of claim 1, wherein the probe pulse is delivered at least 1 ms after the end of the therapeutic pulse.

9. The method of claim 1, wherein measuring the neural response comprises:
   settling measurement circuitry prior to the probe pulse by connecting the one or more sense electrodes to the measurement circuitry to allow the measurement circuitry to settle towards a bio-electrically defined steady state;
   recovering charge on the one or more stimulus electrodes by short circuiting the one or more stimulus electrodes to each other;
   keeping the one or more sense electrodes disconnected from the measurement circuitry while delivering the probe pulse;
   imposing a delay during which the one or more stimulus electrodes are open circuited and the one or more sense electrodes are disconnected from the measurement circuitry and from the one or more stimulus electrodes; and
   measuring, after the delay, the neural response by connecting the one or more sense electrodes to the measurement circuitry.

10. An implantable device for applying neural stimulus to neural tissue, the device comprising:
    a plurality of electrodes including one or more stimulus electrodes and one or more sense electrodes;
    a stimulus source for delivering stimulus pulses via the one or more stimulus electrodes to neural tissue;
    measurement circuitry for measuring a neural signal sensed at the one or more sense electrodes; and
    a control unit configured to:
       control the stimulus source to deliver a therapeutic pulse to neural tissue via the one or more stimulus electrodes, the therapeutic pulse having a first pulse width, wherein the therapeutic pulse evokes a neural response;
       control the stimulus source to deliver at least one probe pulse to the neural tissue having a second pulse width after the therapeutic pulse, wherein the second pulse width is less than the first pulse width;
       control the measurement circuitry to measure a neural response subsequent to the therapeutic pulse;
       determine a neural recruitment caused by the therapeutic pulse based on the neural response; and
       determine a parameter for a subsequent therapeutic pulse based on the neural recruitment.

11. The implantable device of claim 10, wherein the first pulse width is in a range of 100-500 μs.

12. The implantable device of claim 10, wherein the control unit is configured to determine the parameter for the subsequent therapeutic pulse by:
    comparing the neural recruitment with a target neural recruitment;
    deriving a command from the comparison; and
    selecting, based on the command, the parameter for the subsequent therapeutic pulse.

13. The implantable device of claim 12, wherein the control unit is configured to select the parameter by refining a parameter for the delivered therapeutic pulse.

14. The implantable device of claim 12, wherein the target neural recruitment is a predetermined neural recruitment.

15. The implantable device of claim 10, wherein the control unit is configured to determine a parameter for a subsequent probe pulse based on the neural recruitment.

16. The implantable device of claim 10, wherein the control unit is configured to control the stimulus source to deliver the probe pulse at least 1 ms after the end of the therapeutic pulse.

17. The implantable device of claim 10, wherein the control unit is configured to control the measurement circuitry to measure the neural response by:
    settling the measurement circuitry prior to the probe pulse by connecting the one or more sense electrodes to the measurement circuitry to allow the measurement circuitry to settle towards a bio-electrically defined steady state, recovering charge on the one or more stimulus electrodes by short circuiting the one or more stimulus electrodes to each other;

keeping the one or more sense electrodes disconnected from the measurement circuitry while delivering the probe pulse, imposing a delay during which the one or more stimulus electrodes are open circuited and the one or more sense electrodes are disconnected from the measurement circuitry and from the one or more stimulus electrodes; and measuring, after the delay, the neural response by connecting the one or more sense electrodes to the measurement circuitry.

18. A method of applying stimulus to a tissue, the method comprising:

delivering a plurality of therapeutic pulses having a first pulse width, wherein the therapeutic pulses evoke neural responses;

delivering a plurality of probe pulses having a second pulse width interleaved with at least some therapeutic pulses of the plurality of therapeutic pulses, wherein the second pulse width is less than the first pulse width, measuring, after a therapeutic pulse of the plurality of therapeutic pulses and prior to a subsequent probe pulse of the plurality of probe pulses, a neural response evoked by the therapeutic pulse;

determining a neural recruitment caused by the therapeutic pulse based on the neural response; and determining a parameter for the subsequent therapeutic pulse based on the neural recruitment.

19. The method of claim 18, wherein the first pulse width is in a range of 100-500 µs.

20. The method of claim 18, wherein the determining the parameter comprises:

comparing the neural recruitment with a target neural recruitment;

deriving, using a controller, a command from the comparison; and selecting, based on the command, the parameter for the subsequent therapeutic pulse.

21. The method of claim 20, wherein the selecting the parameter comprises refining a parameter for the preceding delivered therapeutic pulse.

22. The method of claim 20, wherein the target neural recruitment is a predetermined neural recruitment.

23. An implantable device for applying neural stimulus to neural tissue, the device comprising:

a plurality of electrodes including one or more stimulus electrodes and one or more sense electrodes;

a stimulus source for delivering stimulus pulses via the one or more stimulus electrodes to neural tissue;

measurement circuitry for measuring a neural signal sensed at the one or more sense electrodes: and a control unit configured to:

control the stimulus source to deliver a plurality of therapeutic pulses to neural tissue via the one or more stimulus electrodes, the therapeutic pulses having a first pulse width, wherein the therapeutic pulses evoke neural responses;

control the stimulus source to deliver a plurality of probe pulses to the neural tissue having a second pulse width interleaved with at least some therapeutic pulses of the plurality of therapeutic pulses, wherein the second pulse width is less than the first pulse width;

control the measurement circuitry to measure, after a therapeutic pulse of the plurality of therapeutic pulses and prior to a subsequent probe pulse of the plurality of probe pulses, the neural response evoked by the therapeutic pulse;

determine a neural recruitment caused by the therapeutic pulse based on the neural response; and determining a parameter for the subsequent therapeutic pulse based on the neural recruitment.

24. The implantable device of claim 23, wherein the first pulse width is in a range of 100-500 µs.

25. The implantable device of claim 23, wherein the control unit is configured to determine the parameter for the subsequent therapeutic pulse by:

comparing the neural recruitment with a target neural recruitment;

deriving a command from the comparison; and selecting, based on the command, the parameter for the subsequent therapeutic pulse.

26. The implantable device of claim 25, wherein the control unit is configured to select the parameter by refining a parameter for the preceding delivered therapeutic pulse.

27. The implantable device of claim 25, wherein the target neural recruitment is a predetermined neural recruitment.

28. The implantable device of claim 23, wherein the control unit is configured to determine a parameter for a subsequent probe pulse based on the neural recruitment.

29. The implantable device of claim 23, wherein the control unit is configured to control the stimulus source to deliver each probe pulse at least 1 ms after the end of the preceding therapeutic pulse.

* * * * *